United States Patent
Shuh et al.

(10) Patent No.: US 12,285,161 B2
(45) Date of Patent: Apr. 29, 2025

(54) SUPPORT APPARATUS FOR A MEDICAL RETRACTOR DEVICE

(71) Applicant: Intuitive Surgical Operations, Inc., Sunnyvale, CA (US)

(72) Inventors: Christina J. Shuh, Snohomish, WA (US); Ralph Wadensweiler, Sunnyvale, CA (US); Kyle R. Miller, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 549 days.

(21) Appl. No.: 17/538,220

(22) Filed: Nov. 30, 2021

(65) Prior Publication Data

US 2022/0087668 A1  Mar. 24, 2022

Related U.S. Application Data

(63) Continuation of application No. 16/682,599, filed on Nov. 13, 2019, now Pat. No. 11,213,287.
(Continued)

(51) Int. Cl.
*A61B 17/02* (2006.01)
*A61B 17/00* (2006.01)
*A61B 34/35* (2016.01)

(52) U.S. Cl.
CPC .. *A61B 17/0218* (2013.01); *A61B 2017/0023* (2013.01); *A61B 2017/00867* (2013.01); *A61B 2017/0225* (2013.01); *A61B 34/35* (2016.02)

(58) Field of Classification Search
CPC .................. A61B 17/0218; A61B 2017/0225
(Continued)

(56) References Cited

U.S. PATENT DOCUMENTS 3,841,317 A * 10/1974 Awais ................ A61B 1/00142
600/203
5,052,402 A   10/1991 Bencini et al.
(Continued)

FOREIGN PATENT DOCUMENTS

DE       19537320 A1    4/1997
EP       1151723 A2    11/2001
(Continued)

OTHER PUBLICATIONS

Bean E., et al., "Evaluation of a Novel Atrial Retractor for Exposure of the Mitral Valve in a Porcine Model," The Journal of Thoracic and Cardiovascular Surgery, Dec. 2008, vol. 136 (6), pp. 1492-1495.
(Continued)

*Primary Examiner* — Ellen C Hammond
*Assistant Examiner* — Tara Rose E Carter

(57) ABSTRACT

A support apparatus for a medical device includes a first sleeve, a second sleeve, and a flexible contact member. The first sleeve is configured to be coupled to a first tool member of an end effector assembly that includes the first tool member, a second tool member, and a clevis, in which the first and second tool members are each rotatably coupled to the clevis such that second tool member can be moved relative to the first tool member between a first and a second orientation. The second sleeve is configured to be coupled to the second tool member. The flexible contact member is coupled to the first sleeve and the second sleeve, and is configured be moved between a collapsed configuration when the second tool member is in the first orientation and an expanded configuration when the second tool member is in the second orientation.

16 Claims, 24 Drawing Sheets

Related U.S. Application Data

(60) Provisional application No. 62/767,682, filed on Nov. 15, 2018.

(58) Field of Classification Search
USPC .................................................. 600/201–245
See application file for complete search history.

(56) References Cited

U.S. PATENT DOCUMENTS

| | | | |
|---|---|---|---|
| 5,318,589 A | 6/1994 | Lichtman | |
| 5,373,854 A | 12/1994 | Kolozsi | |
| 5,395,375 A | 3/1995 | Turkel et al. | |
| 5,396,900 A | 3/1995 | Slater et al. | |
| 5,476,479 A | 12/1995 | Green et al. | |
| 5,482,054 A | 1/1996 | Slater et al. | |
| 5,490,819 A | 2/1996 | Nicholas et al. | |
| 5,496,317 A | 3/1996 | Goble et al. | |
| 5,496,347 A | 3/1996 | Hashiguchi et al. | |
| 5,527,339 A | 6/1996 | Koscher et al. | |
| 5,575,805 A | 11/1996 | Li | |
| 5,582,617 A | 12/1996 | Klieman et al. | |
| 5,722,935 A | 3/1998 | Christian | |
| 5,735,845 A * | 4/1998 | Zupkas | A61B 90/04 128/898 |
| 5,792,165 A | 8/1998 | Klieman et al. | |
| 5,807,243 A * | 9/1998 | Vierra | A61B 17/0469 600/235 |
| 5,855,583 A | 1/1999 | Wang et al. | |
| 5,906,630 A | 5/1999 | Anderhub et al. | |
| 5,964,780 A | 10/1999 | Balazs | |
| 5,968,074 A | 10/1999 | Prestel | |
| 6,206,903 B1 | 3/2001 | Ramans | |
| 6,214,010 B1 | 4/2001 | Farley et al. | |
| 6,273,860 B1 | 8/2001 | Kostylev et al. | |
| 6,309,397 B1 | 10/2001 | Julian et al. | |
| 6,331,181 B1 | 12/2001 | Tierney et al. | |
| 6,368,290 B1 | 4/2002 | Baska | |
| 6,394,998 B1 | 5/2002 | Wallace et al. | |
| 6,554,844 B2 | 4/2003 | Lee et al. | |
| 6,623,482 B2 | 9/2003 | Pendekanti et al. | |
| 6,644,532 B2 | 11/2003 | Green et al. | |
| 6,685,698 B2 | 2/2004 | Morley et al. | |
| 6,817,974 B2 | 11/2004 | Cooper et al. | |
| 6,840,938 B1 | 1/2005 | Morley et al. | |
| 6,843,793 B2 | 1/2005 | Brock et al. | |
| 6,949,106 B2 | 9/2005 | Brock et al. | |
| 6,994,708 B2 | 2/2006 | Manzo | |
| 7,083,571 B2 | 8/2006 | Wang et al. | |
| 7,090,683 B2 | 8/2006 | Brock et al. | |
| 7,125,403 B2 | 10/2006 | Julian et al. | |
| 7,147,650 B2 | 12/2006 | Lee | |
| 7,169,141 B2 | 1/2007 | Brock et al. | |
| 7,214,230 B2 | 5/2007 | Brock et al. | |
| 7,338,513 B2 | 3/2008 | Lee et al. | |
| 7,371,210 B2 | 5/2008 | Brock et al. | |
| 7,445,598 B2 * | 11/2008 | Orban, III | A61B 17/0218 606/198 |
| 7,608,083 B2 | 10/2009 | Lee et al. | |
| 7,824,401 B2 | 11/2010 | Manzo et al. | |
| 7,935,130 B2 | 5/2011 | Williams | |
| 8,479,969 B2 | 7/2013 | Shelton, IV | |
| 8,568,443 B1 | 10/2013 | Jackman et al. | |
| 8,597,182 B2 | 12/2013 | Stein et al. | |
| 8,758,392 B2 | 6/2014 | Crainich | |
| 8,800,838 B2 | 8/2014 | Shelton, IV | |
| 9,028,494 B2 | 5/2015 | Shelton, IV et al. | |
| 9,078,684 B2 | 7/2015 | Williams | |
| 9,204,923 B2 | 12/2015 | Manzo et al. | |
| 9,339,341 B2 | 5/2016 | Cooper | |
| 9,456,839 B2 | 10/2016 | Cooper | |
| 9,554,790 B2 | 1/2017 | Bailey et al. | |
| 9,615,846 B2 | 4/2017 | Prestel | |
| 9,869,339 B2 | 1/2018 | Zimmerman et al. | |
| 9,918,731 B2 | 3/2018 | Cooper et al. | |
| 10,130,366 B2 | 11/2018 | Shelton, IV et al. | |
| 10,667,873 B2 | 6/2020 | Wallace | |
| 10,905,411 B2 | 2/2021 | Racenet et al. | |
| 11,213,287 B2 | 1/2022 | Shuh et al. | |
| 11,291,514 B2 | 4/2022 | Shuh et al. | |
| 2003/0069477 A1 * | 4/2003 | Raisman | A61B 1/303 600/220 |
| 2004/0087940 A1 | 5/2004 | Jahns et al. | |
| 2004/0260198 A1 | 12/2004 | Rothberg et al. | |
| 2006/0074415 A1 | 4/2006 | Scott et al. | |
| 2006/0184198 A1 | 8/2006 | Bales et al. | |
| 2007/0208375 A1 | 9/2007 | Nishizawa et al. | |
| 2008/0046122 A1 | 2/2008 | Manzo et al. | |
| 2008/0065102 A1 | 3/2008 | Cooper | |
| 2008/0065105 A1 | 3/2008 | Larkin et al. | |
| 2008/0196533 A1 | 8/2008 | Bergamasco et al. | |
| 2009/0088774 A1 | 4/2009 | Swarup et al. | |
| 2009/0110533 A1 | 4/2009 | Jinno et al. | |
| 2009/0131975 A1 | 5/2009 | Ahlberg et al. | |
| 2009/0198272 A1 | 8/2009 | Kerver et al. | |
| 2009/0326530 A1 | 12/2009 | Orban, III et al. | |
| 2010/0030238 A1 | 2/2010 | Viola et al. | |
| 2011/0295269 A1 | 12/2011 | Swensgard et al. | |
| 2011/0295270 A1 | 12/2011 | Giordano et al. | |
| 2012/0116433 A1 | 5/2012 | Houser et al. | |
| 2013/0144395 A1 | 6/2013 | Stefanchik et al. | |
| 2014/0005662 A1 | 1/2014 | Shelton, IV | |
| 2014/0005678 A1 | 1/2014 | Shelton, IV et al. | |
| 2014/0005708 A1 | 1/2014 | Shelton, IV | |
| 2014/0073856 A1 | 3/2014 | Stein et al. | |
| 2014/0100558 A1 | 4/2014 | Schmitz et al. | |
| 2014/0243850 A1 | 8/2014 | Sadaka | |
| 2014/0276956 A1 | 9/2014 | Crainich et al. | |
| 2015/0150584 A1 | 6/2015 | Van Tol et al. | |
| 2015/0150635 A1 | 6/2015 | Kilroy et al. | |
| 2015/0157355 A1 | 6/2015 | Price et al. | |
| 2016/0000423 A1 | 1/2016 | Shields et al. | |
| 2016/0287279 A1 | 10/2016 | Bovay et al. | |
| 2016/0303743 A1 | 10/2016 | Rockrohr | |
| 2017/0333037 A1 | 11/2017 | Wellman et al. | |
| 2018/0168572 A1 | 6/2018 | Burbank | |
| 2018/0206904 A1 | 7/2018 | Felder et al. | |
| 2019/0059988 A1 | 2/2019 | Davison et al. | |
| 2019/0099227 A1 | 4/2019 | Rockrohr | |
| 2019/0192137 A1 | 6/2019 | Shelton, IV et al. | |
| 2019/0223960 A1 | 7/2019 | Chaplin et al. | |
| 2019/0231374 A1 | 8/2019 | Kimura et al. | |
| 2019/0374240 A1 | 12/2019 | Brodbeck et al. | |
| 2019/0374297 A1 | 12/2019 | Wallace et al. | |
| 2020/0015807 A1 | 1/2020 | Limon et al. | |
| 2020/0022765 A1 | 1/2020 | Limon et al. | |
| 2020/0054405 A1 | 2/2020 | Schuh et al. | |
| 2020/0054408 A1 | 2/2020 | Schuh et al. | |
| 2020/0138531 A1 | 5/2020 | Chaplin | |
| 2020/0155136 A1 | 5/2020 | Shuh et al. | |
| 2020/0155253 A1 | 5/2020 | Shuh et al. | |
| 2021/0177534 A1 | 6/2021 | Park | |

FOREIGN PATENT DOCUMENTS

| | | |
|---|---|---|
| WO | WO-2016025132 A1 | 2/2016 |
| WO | WO-2016045041 A1 | 3/2016 |

OTHER PUBLICATIONS

Lassooij J., et al., "A Statically Balanced and Bi-stable Compliant End Effector Combined with a Laparoscopic 2DoF Robotic Arm," Journal of Mechanical Sciences, 2012, vol. 3, pp. 85-93.

Litvin F.L., et al., "Face Gear Drive with Helical Involute Pinion: Geometry, Generation by a Shaper and a Worm, Avoidance of Singularities and Stress Analysis," NASA/CR—2005-213443, ARL-CR-557, Feb. 2005, 62 pages.

Non-Final Office Action for U.S. Appl. No. 16/682,599 mailed Apr. 27, 2021, 7 pages.

Smith J.M., et al., "Totally Endoscopic Mitral Valve Repair Using a Robotic-controlled Atrial Retractor," The Annals of Thoracic Surgery, Aug. 2007, vol. 84 (2), pp. 633-637.

(56) References Cited

OTHER PUBLICATIONS

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

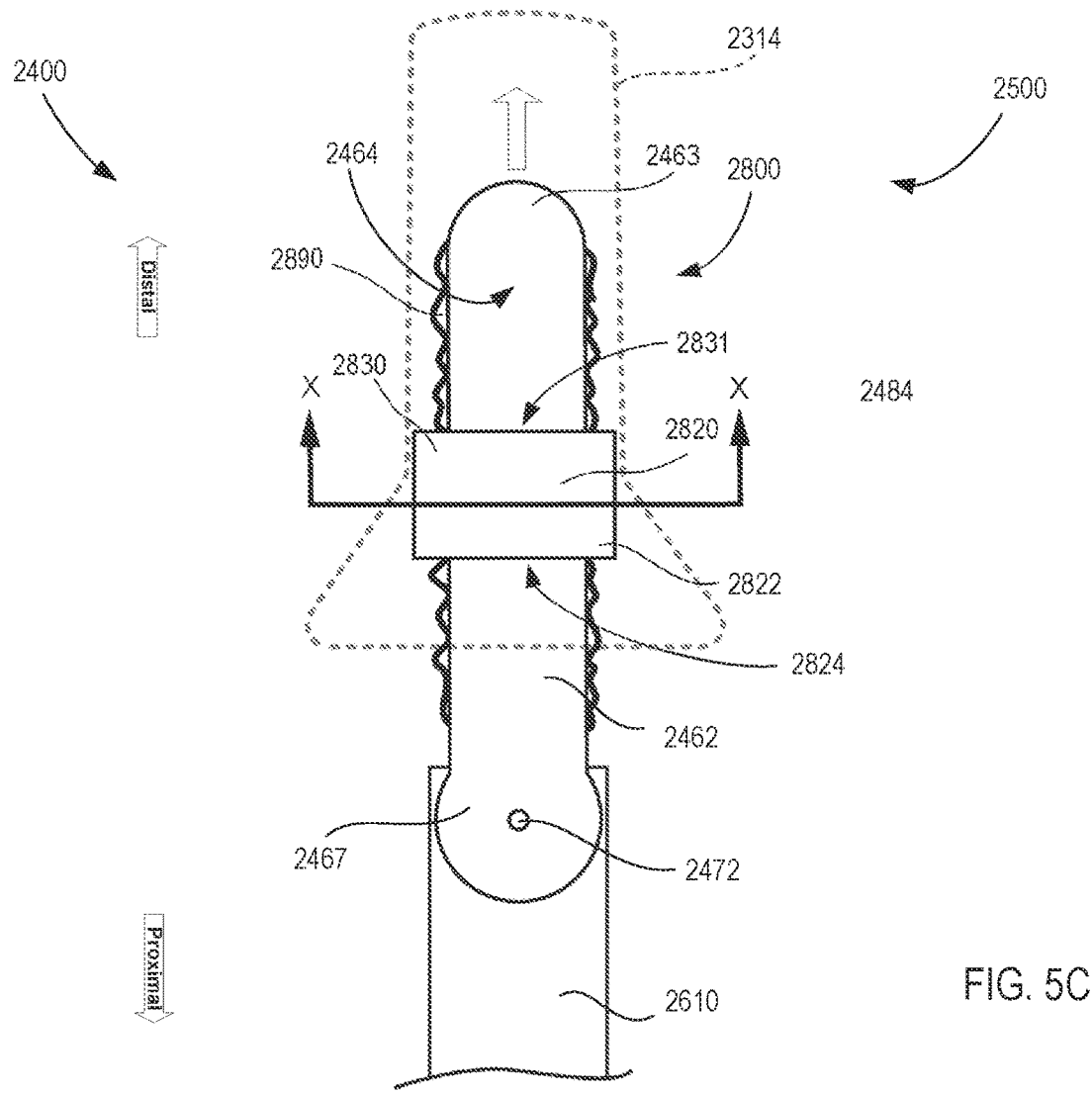
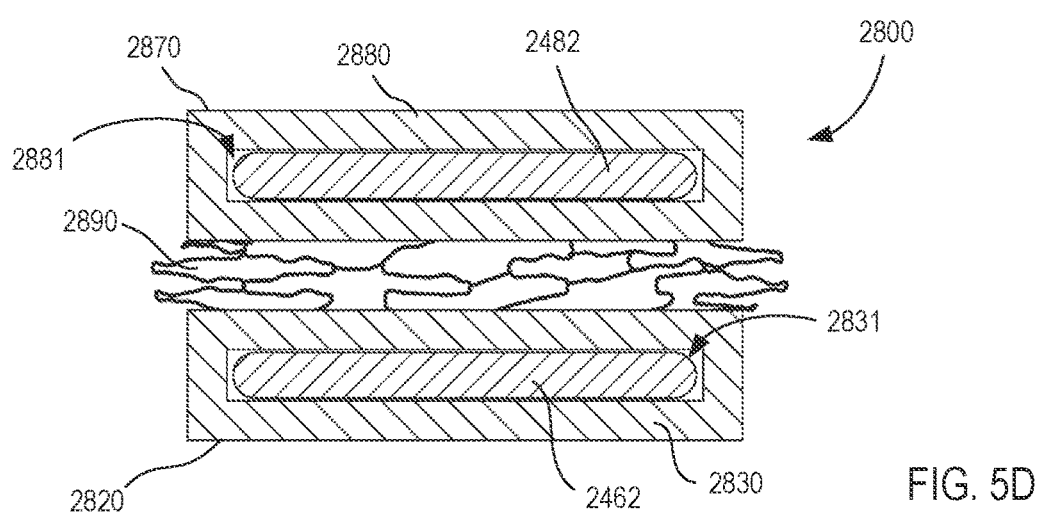
FIG. 5C
FIG. 5D

SUPPORT APPARATUS FOR A MEDICAL RETRACTOR DEVICE

CROSS-REFERENCE TO RELATED APPLICATION

This application is a continuation of U.S. patent application Ser. No. 16/682,599 (filed Nov. 13, 2019) (entitled "Support Apparatus for a Medical Retractor Device"), which claims benefit of priority to U.S. Provisional Application No. 62/767,682 (filed Nov. 15, 2018) (entitled "Support Apparatus for Medical Retractor Device"), each of which is incorporated herein by reference in its entirety.

BACKGROUND

The embodiments described herein relate to medical tools and particularly to surgical instruments, and more particularly relate to endoscopic tools. Further, the embodiments described herein relate to endoscopic surgical instruments configured to perform surgical retractor functions, such as holding back tissue during surgical procedures, removing tissue, and moving organs. More particularly, the embodiments described herein relate to a support apparatus configured to be coupled to a surgical retractor such that the support apparatus modifies engagement of the surgical retractor with tissue or organs.

Known techniques for Minimally Invasive Surgery (MIS) employ instruments to manipulate tissue that can be either manually controlled or controlled via computer-assisted teleoperation. Many known MIS instruments include a therapeutic or diagnostic end effector (e.g., forceps, a cutting tool, a tissue retractor, or a cauterizing tool) mounted on a wrist mechanism at the distal end of an extension (also referred to herein as the main tube or shaft). During an MIS procedure, the end effector, wrist mechanism, and the distal end of the main tube can be inserted into a small incision or a natural orifice of a patient to position the end effector at a work site within the patient's body. The optional wrist mechanism can be used to change the end effector's orientation with respect to the main tube to perform the desired procedure at the work site. Known wrist mechanisms generally provide the desired degrees of freedom (DOFs) for movement of the end effector. For example, for forceps or other grasping tools, known wrist mechanisms are often able to change the pitch and yaw of the end effector with reference to the main tube. A wrist may optionally provide a roll DOF for the end effector, or the roll DOF may be implemented by rolling the main tube. An end effector may optionally have additional mechanical DOFs, such as grip, knife blade, or retractor motion. In some instances, wrist and end effector mechanical DOFs may be combined. For example, U.S. Pat. No. 5,792,135 (filed May 16, 1997) discloses a mechanism in which wrist and end effector grip DOFs are combined.

Known end effectors can include one or more retractor tools to perform retractor functions including engaging tissue or organs to move, hold up, and remove tissue or organs. The retractor tools are designed for engaging tissue or organs in a surgical environment in cooperation with other MIS instruments as part of a clinical procedure. This includes engaging various types of tissues and organs for many different types of procedures. For example, surgical retractors are used to perform preparation functions, such as moving tissue or organs to provide access for other MIS tools, and concomitant functions, such as moving excised tissue away from active surgery functions. Further, surgical retractors are used to perform cooperative functions with other MIS tools, such as dynamically exposing valve structures during mitral valve repair procedures.

Conventional surgical retractor tools include surgical retractors having a single flexible retractor member, in which the single flexible member is retained in a collapsed, compact configuration for insertion through a cannula into the surgical environment. The single flexible member expands therein into an expanded, functional configuration to perform retractor functions. The retractor member for these devices expands into a framework structure or a lattice-type structure that engages tissue or organs to perform retractor functions. These devices provide fixed-shape and fixed-sized retractor members, which can create challenges from the lack of adjustment options. Further, these devices engage portions of the tissue and organs that interface with the framework members or lattice structure members without engaging intermediate portions, which can create challenges related to concentrated forces being applied at the engagement members.

Conventional surgical retractor tools further include surgical retractors having multiple movable retractor blades, in which multiple movable retractor blades are aligned in a compact configuration for insertion through a cannula into the surgical environment. The movable retractor blades move therein into an expanded configuration to perform retractor functions. The retractor blades expand by spreading apart into a fan-like arrangement of blades that engages tissue or organs to perform retractor functions. The expanded arrangements of retractor blades can be adjustable. Challenges can occur with lack of tissue engagement in spaces between the retractor blades with tissues or organs when in expanded configurations, and with concentrated forces being applied along the retractor blades.

Thus, a need exists for improved endoscopic retractor tools and support devices for surgical retractors. Improvements may include removable devices configured to be coupled to endoscopic tools to modify engagement of the tools with tissue or organs for performing retractor functions.

SUMMARY

This summary introduces certain aspects of the embodiments described herein to provide a basic understanding. This summary is not an extensive overview of the inventive subject matter, and it is not intended to identify key or critical elements or to delineate the scope of the inventive subject matter.

In some embodiments, an apparatus includes a first sleeve, a second sleeve, and a flexible contact member. The first sleeve is configured to be coupled to a first tool member of an end effector assembly, which includes the first tool member, a second tool member, and a clevis. The first tool member and the second tool member are each rotatably coupled to the clevis such that second tool member can be moved relative to the first tool member between a first orientation and a second orientation. The second sleeve is configured to be coupled to the second tool member. The flexible contact member is coupled to the first sleeve and the second sleeve. The flexible contact member is configured be moved between a collapsed configuration when the second tool member is in the first orientation and an expanded configuration when the second tool member is in the second orientation. In some embodiments, the flexible contact member includes an elastomeric sheet. In some embodiments, the flexible contact member is a mesh and defines a pattern of openings. The plurality of openings includes a pattern of slots. In some embodiments, the flexible contact member includes a first surface and a reverse second surface. At least one of the first or second surfaces has a surface texture with raised portions to contact tissue.

In some embodiments, the first tool member is a first retractor blade having a first tissue contact surface, and the second tool member is a second retractor blade having second tissue contact surface. The first sleeve is configured to be placed about a portion of the first tissue contact surface, and the second sleeve is configured to be placed about a portion of the second tissue contact surface. In some embodiments, the first sleeve defines a first pocket configured to receive the first tool member and surround the portion of the first tissue contact surface, and the second sleeve defines a second pocket configured to receive the second tool member and surround the portion of the second tissue contact surface. In some embodiments, the first pocket has a first interior dimension less than an exterior dimension of the first tool member, and the second pocket has a second interior dimension less than an exterior dimension of the second tool member. The first interior surface at the first interior dimension is a first retention portion, and the second interior surface at the second interior dimension is a second retention portion. In some embodiments, the first interior dimension is an interior height of the first pocket, and a second interior dimension is an interior height of the second pocket. The exterior dimension of the first tool member is a first height at a distal end of the tool member, and the exterior dimension of the second tool member is a second height at a distal end of the tool member. In some embodiments, a distal end of the first tool member includes a first curved portion extending from the first tool member at the first height.

In some embodiments, the first and second sleeves are each configured to extend along at least half of a length of the first and second retractor blades, respectively. In some embodiments, the first and second sleeves are each configured to extend along at least three-quarters of a length of the first and second retractor blades, respectively. In some embodiments, each of the first and second sleeves are configured to be removably coupled about a corresponding one of the first and second retractor blades.

In some embodiments, the end effector assembly further includes a third retractor blade, and the flexible contact member is configured to extend across a flat surface of the third retractor blade when the second tool member is in the second orientation. The apparatus can further include a third sleeve configured to be coupled to the third retractor blade, and the flexible contact member can contact member includes a first portion coupled to the first sleeve and the third sleeve, and a second portion coupled to the second sleeve and the third sleeve. In some embodiments, the first sleeve includes a first retention portion, and the second sleeve includes a second retention portion. The first retention portion is configured to engage the first retractor blade to retain the first sleeve about the first tissue contact surface. The second retention portion is configured to engage the second retractor blade to retain the second sleeve about the second tissue contact surface. When the first sleeve is in a first position about the portion of the first tissue contact surface, the first retention portion can be configured to interfere with the first retractor blade to prevent removal of the first sleeve from the first position. When the second sleeve is in a second position about the portion of the second tissue contact surface, the second retention portion can be configured to interfere with the second retractor blade to prevent removal of the second sleeve from the second position.

In some embodiments, the flexible contact member includes a plurality of elongate connectors forming an interlaced structure with each other, in which the elongate connectors extend between the first sleeve and the second sleeve. In some embodiments, the flexible contact member is a mesh and defines a plurality of holes. The plurality of holes can include a pattern of spaced apart slots. In some embodiments, the flexible contact member includes a first surface and an opposite (or reverse) second surface, and at least one of the first surface and second surface has a surface texture with raised portions configured to contact tissue.

In some embodiments, a method includes coupling a first connection member of a tissue manipulation accessory to a first tool member of an end effector assembly that includes the first tool member, a second tool member, and a clevis. The first tool member and the second tool member are each rotatably coupled to the clevis such that second tool member can be moved relative to the first tool member between an open first orientation and a closed second orientation. The coupling is performed when the second tool member is in the open first orientation with respect to the first tool member. The method further includes rotating, after the coupling, at least one of the first tool member or the second tool member to place the second tool member in the closed second orientation, and inserting the end effector assembly and the tissue manipulation accessory into a cannula when the second tool member is in the closed second orientation. The method can further include introducing, after the inserting, the end effector assembly and the tissue manipulation accessory into a body cavity, as well as rotating, after the inserting, at least one of the first tool member or the second tool member to move the second tool member from the closed second orientation towards the open first orientation. Further, the method can include coupling, while the second tool member is in the open first orientation, a second connection member of the tissue manipulation accessory to the second tool member of the end effector assembly.

In some embodiments, the first connection member is a first sleeve, the second connection member is a second sleeve, the first tool member includes a first coupling portion that retains the first sleeve, and the second tool member includes a second coupling portion that retains the second sleeve. In addition, the coupling the first connection member includes sliding the first sleeve over the first coupling portion of the first tool member, and the coupling the second connection member includes sliding the second sleeve over the second coupling portion of the second tool member. In some embodiments, the end effector assembly is a tissue retractor assembly, the first tool member is a first blade, and the second tool member is a second blade.

In some embodiments, an apparatus includes a first removable connector, a second removable connector, and a flexible contact member. The first removable connector is configured to be removably mated to a first blade of a tissue retractor assembly. The tissue retractor assembly includes the first blade, a second blade, and a clevis. The first blade and the second blade are each rotatably coupled to the clevis such that second blade can be moved relative to the first blade between a first orientation and a second orientation. The second removable connector is configured to be removably mated to the second blade. The flexible contact member is coupled to the first removable connector and the second removable connector. The flexible contact member is configured to be moved between a collapsed configuration when the second blade is in the first orientation and an expanded configuration when the second blade is in the second orientation.

In some embodiments, the first removable connector is a clip defining a pocket configured to receive the first blade. The clip can be configured to form an interference fit around a portion of the first blade. The first blade can define an opening configured to retain a mating portion of the first removable connector. The opening can be a slot and the mating portion can include a shaped protrusion. The shaped protrusion can be hook shaped. In some embodiments, the flexible contact member includes a plurality of elongate connectors forming an interlaced structure with each other, in which the elongate connectors extend between the first sleeve member and the second sleeve member. In some embodiments, the interlaced structure forms a mesh sheet. In some embodiment, the flexible contact member is a mesh sheet and the mesh sheet defines a plurality of holes. In some embodiments, the flexible contact sheet includes a first surface and a reverse second surface. At least one of the first or second surfaces has a surface texture with raised portions to contact tissue.

Other medical devices, support devices for medical devices, related components, medical device systems, and/or methods according to embodiments will be or become apparent to one with skill in the art upon review of the following drawings and detailed description. It is intended that all such additional medical devices, related components, medical device systems, and/or methods included within this description be within the scope of this disclosure.

BRIEF DESCRIPTION OF THE DRAWINGS

FIG. 5C is a diagrammatic front view of the removable support apparatus assembly of FIG. 5B, which is shown in a third orientation.

FIG. 5D is a cross-sectional view of removable support apparatus assembly shown in FIG. 5C, as viewed from line X-X shown in FIG. 5C.

DETAILED DESCRIPTION

Figure 1:
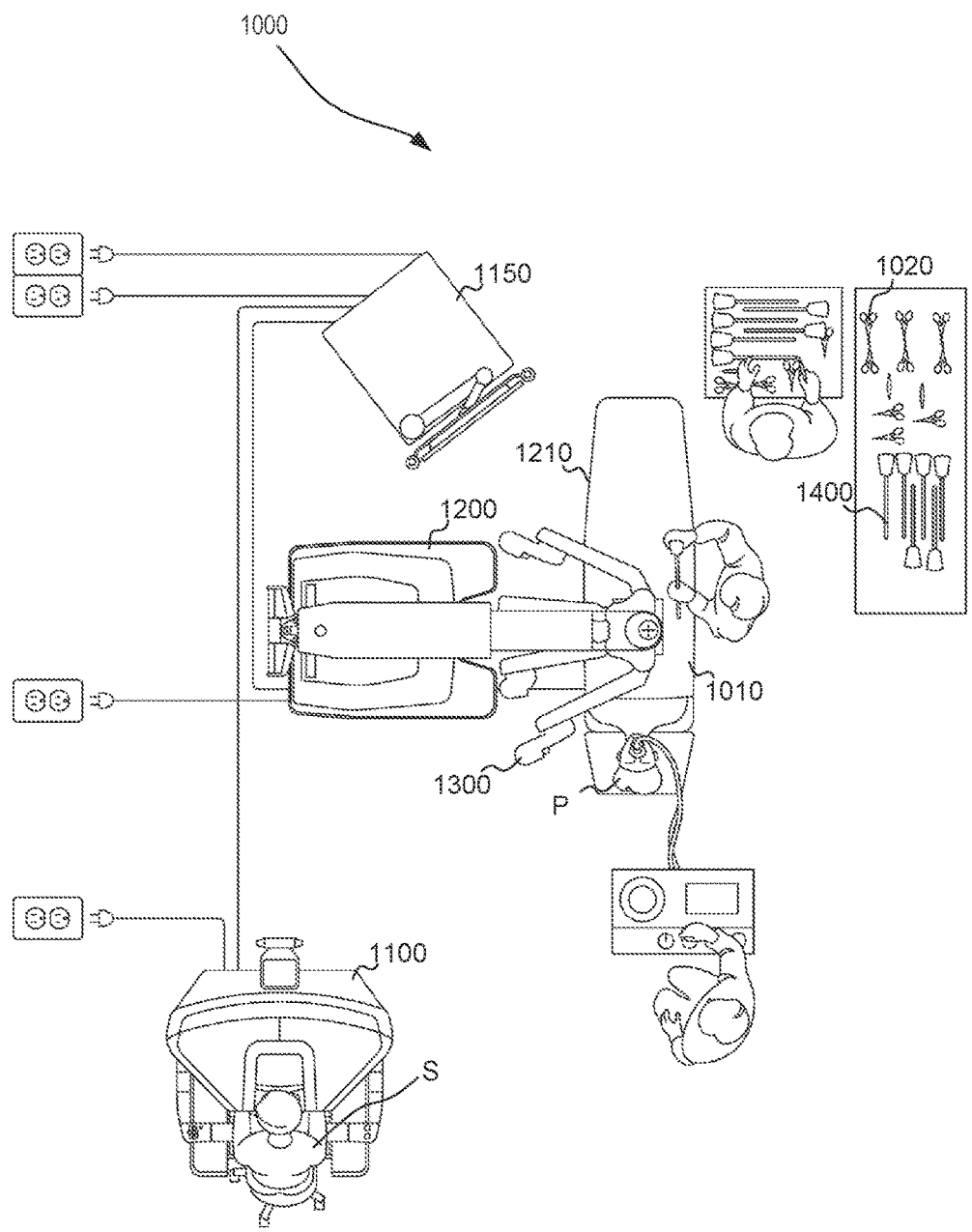
FIG. 1 is a plan view of a minimally invasive teleoperated medical system according to an embodiment, being used to perform a medical procedure such as surgery.

The embodiments described herein can advantageously be used in a wide variety of grasping, cutting, and manipulating operations associated with minimally invasive surgery. In particular, the instruments described herein can be low-cost, disposable instruments that facilitate being used for only one procedure. Furthermore, instruments described herein can be multi-functional MIS instruments configured to multiple combinations of clinical functions that are each performed by single MIS instruments and can do so without requiring larger incisions or cannula diameters than the single MIS instruments. In addition, multi-functional instruments described herein can be configured to perform the various combinations of multiple clinical functions without loss of operability, maneuverability, or clinical functionality compared with corresponding single MIS instruments that would be required to provide the same functionality. As described herein, the multi-functional instruments can be driven by various drive components, such as combinations of motors, gears, actuators, transmission members, etc. Further, the multi-functional instruments described herein can include one or more cables (which act as tension members) that can be moved to actuate the end effector of a multi-functional MIS instrument to perform the various clinical functions and move with multiple degrees of freedom.

As used herein, the term "about" when used in connection with a referenced numeric indication means the referenced numeric indication plus or minus up to 10 percent of that referenced numeric indication. For example, the language "about 50" covers the range of 45 to 55. Similarly, the language "about 5" covers the range of 4.5 to 5.5.

As used herein, the term "target workspace" refers to anything within or pertaining to the endoscopic work cavity including the body of the patient, P, tissues and organs within the cavity, and tissue defining the cavity, and also to support structures for the MIS procedure including a cover and cannula supports, instruments and related attachments or medical implements including needles, suture materials, implants, meshes, etc. As used herein, the term "target tissue" refers to any tissue or organ that interacts with the target workspace including tissues and organs of the patient, P, natural tissues and organs introduced to the target workspace including natural transplant tissues and organs, artificial tissues and organs including mechanical or electromechanical organs, and tissue and organ assist devices such as pacemakers, mesh material, artificial skin and the like.

As used herein, a surgical "retractor" or "retractor-type" tool or clinical instrument refers to a medical instrument having contact surfaces that are configured to engage organs, tissues and/or portions of a surgical cavity or wound to thereby move, hold, lift, retain or otherwise engage, interface or make contact with the target tissue and perform clinical retractor-type functions as appropriate for the surgical environment. Thus, as described in detail below, instrument 4400 can be configured to engage target tissue and perform effective retractor functions via controlling its contact with a target tissue. As further described below, instrument 4400 can further be controlled to provide enhanced and additional types of clinical functions along with performing its primary retractor-type functions.

The term "flexible" in association with a part, such as a mechanical structure, component, or component assembly, should be broadly construed. In essence, the term means the part can be repeatedly bent and restored to an original shape without harm to the part. Certain flexible components can also be resilient. For example, a component (e.g., a flexure) is said to be resilient if possesses the ability to absorb energy when it is deformed elastically, and then release the stored energy upon unloading (i.e., returning to its original state). Many "rigid" objects have a slight inherent resilient "bendiness" due to material properties, although such objects are not considered "flexible" as the term is used herein.

A flexible part may have infinite degrees of freedom (DOF's). Flexibility is an extensive property of the object being described, and thus is dependent upon the material from which the object is formed as well as certain physical characteristics of the object (e.g., cross-sectional shape, length, boundary conditions, etc.). For example, the flexibility of an object can be increased or decreased by selectively including in the object a material having a desired modulus of elasticity, flexural modulus, and/or hardness. The modulus of elasticity is an intensive property of (i.e., is intrinsic to) the constituent material and describes an object's tendency to elastically (i.e., non-permanently) deform in response to an applied force. A material having a high modulus of elasticity will not deflect as much as a material having a low modulus of elasticity in the presence of an equally applied stress. Thus, the flexibility of the object can be decreased, for example, by introducing into the object and/or constructing the object of a material having a relatively high modulus of elasticity. Examples of such parts include closed, bendable tubes (made from, e.g., NITINOL®, polymer, soft rubber, and the like), helical coil springs, etc. that can be bent into various simple or compound curves, often without significant cross-sectional deformation.

Other flexible parts may approximate such an infinite-DOF part by using a series of closely spaced components that are similar to a serial arrangement of short, connected links as snake-like "vertebrae." In such a vertebral arrangement, each component is a short link in a kinematic chain, and movable mechanical constraints (e.g., pin hinge, cup and ball, live hinge, and the like) between each link may allow one (e.g., pitch) or two (e.g., pitch and yaw) DOFs of relative movement between the links. A short, flexible part may serve as, and be modeled as, a single mechanical constraint (a joint) that provides one or more DOF's between two links in a kinematic chain, even though the flexible part itself may be a kinematic chain made of several coupled links having multiple DOFs, or an infinite-DOF link.

As used in this specification and the appended claims, the word "distal" refers to direction towards a work site, and the word "proximal" refers to a direction away from the work site. Thus, for example, the end of a tool that is closest to the target tissue would be the distal end of the tool, and the end opposite the distal end (i.e., the end manipulated by the user or coupled to the actuation shaft) would be the proximal end of the tool.

Further, specific words chosen to describe one or more embodiments and optional elements or features are not intended to limit the invention. For example, spatially relative terms—such as "beneath", "below", "lower", "above", "upper", "proximal", "distal", and the like—may be used to describe the relationship of one element or feature to another element or feature as illustrated in the figures. These spatially relative terms are intended to encompass different positions (i.e., translational placements) and orientations (i.e., rotational placements) of a device in use or operation in addition to the position and orientation shown in the figures. For example, if a device in the figures were turned over, elements described as "below" or "beneath" other elements or features would then be "above" or "over" the other elements or features. Thus, the term "below" can encompass both positions and orientations of above and below. A device may be otherwise oriented (e.g., rotated 90 degrees or at other orientations) and the spatially relative descriptors used herein interpreted accordingly. Likewise, descriptions of movement along (translation) and around (rotation) various axes includes various spatial device positions and orientations. The combination of a body's position and orientation define the body's pose.

Similarly, geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

In addition, the singular forms "a", "an", and "the" are intended to include the plural forms as well, unless the context indicates otherwise. The terms "comprises", "includes", "has", and the like specify the presence of stated features, steps, operations, elements, components, etc. but do not preclude the presence or addition of one or more other features, steps, operations, elements, components, or groups.

Unless indicated otherwise, the terms apparatus, medical device, instrument, and variants thereof, can be interchangeably used.

Aspects of the invention are described primarily in terms of an implementation using a da Vinci® Surgical System, commercialized by Intuitive Surgical, Inc. of Sunnyvale, California. Examples of such surgical systems are the da Vinci Xi® Surgical System (Model IS4000), da Vinci X® Surgical System (Model IS4200), and the da Vinci Si® Surgical System (Model IS3000). Knowledgeable persons will understand, however, that inventive aspects disclosed herein may be embodied and implemented in various ways, including computer-assisted, non-computer-assisted, and hybrid combinations of manual and computer-assisted embodiments and implementations. Implementations on da Vinci® Surgical Systems (e.g., the Model IS4000, the Model IS3000, the Model IS2000, the Model IS1200) are merely presented as examples, and they are not to be considered as limiting the scope of the inventive aspects disclosed herein. As applicable, inventive aspects may be embodied and implemented in both relatively smaller, hand-held, hand-operated devices and relatively larger systems that have additional mechanical support.

FIG. 1 is a plan view illustration of a computer-assisted teleoperation system. Shown is a medical device, which is a Minimally Invasive Robotic Surgical (MIRS) system 1000 (also referred to herein as a minimally invasive teleoperated surgery system), used for performing a minimally invasive diagnostic or surgical procedure on a Patient P who is lying on an Operating table 1010. The system can have any number of components, such as a user control unit 1100 for use by a surgeon or other skilled clinician S during the procedure. The MIRS system 1000 can further include a manipulator unit 1200 (popularly referred to as a surgical robot), and an optional auxiliary equipment unit 1150. The manipulator unit 1200 can include an arm assembly 1300 and a tool assembly removably coupled to the arm assembly. The manipulator unit 1200 can manipulate at least one removably coupled tool assembly 1400 (also referred to herein as a "tool") through a minimally invasive incision in the body or natural orifice of the patient P while the surgeon S views the surgical site and controls movement of the tool 1400 through control unit 1100.

An image of the surgical site is obtained by an endoscope (not shown), such as a stereoscopic endoscope, which can be manipulated by the manipulator unit 1200 to orient the endoscope. The auxiliary equipment unit 1150 can be used to process the images of the surgical site for subsequent display to the Surgeon S through the user control unit 1100. The number of tools 1400 used at one time will generally depend on the diagnostic or surgical procedure and the space constraints within the operating room, among other factors. If it is necessary to change one or more of the instruments 1400 being used during a procedure, an assistant removes the instrument 1400 from the manipulator unit 1200 and replaces it with another instrument 1400 from a tray 1020 in the operating room. Although shown as being used with the instruments 1400, any of the instruments described herein can be used with the MIRS 1000.

Figure 2:
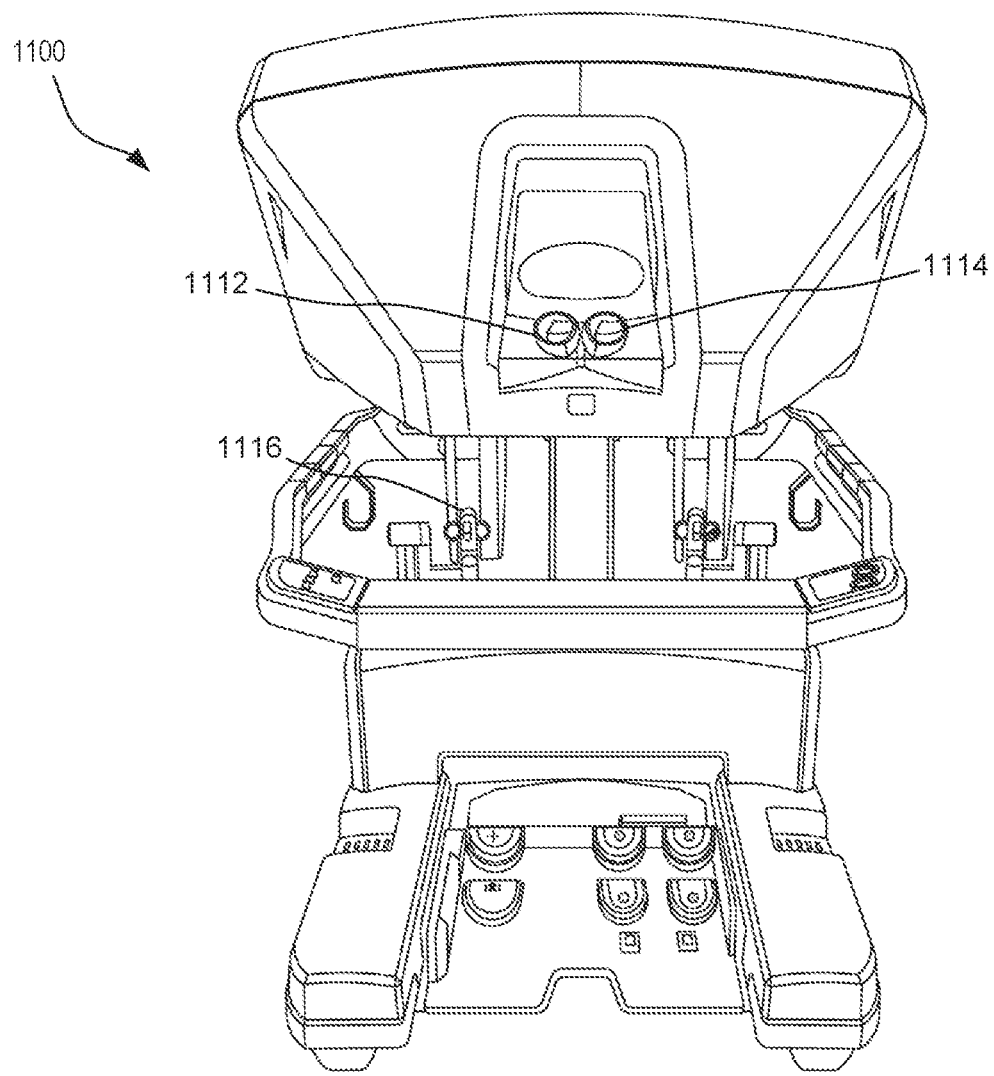
FIG. 2 is a perspective view of an optional auxiliary unit of the minimally invasive tele-operated surgery system shown in FIG. 1.

FIG. 2 is a perspective view of the control unit 1100. The user control unit 1100 includes a left eye display 1112 and a right eye display 1114 for presenting the surgeon S with a coordinated stereo view of the surgical site that enables depth perception. The user control unit 1100 further includes one or more input control devices 1116, which in turn cause the manipulator unit 1200 (shown in FIG. 1) to manipulate one or more tools. The input control devices 1116 provide at least the same degrees of freedom as instruments 1400 with which they are associated to provide the surgeon S with telepresence, or the perception that the input control devices 1116 are integral with (or are directly connected to) the instruments 1400. In this manner, the user control unit 1100 provides the surgeon S with a strong sense of directly controlling the instruments 1400. To this end, position, force, and tactile feedback sensors (not shown) may be employed to transmit position, force, and tactile sensations from the instruments 1400 back to the surgeon's hands through the input control devices 1116.

The user control unit 1100 is shown in FIG. 1 as being in the same room as the patient so that the surgeon S can directly monitor the procedure, be physically present if necessary, and speak to an assistant directly rather than over the telephone or other communication medium. In other embodiments however, the user control unit 1100 and the surgeon S can be in a different room, a completely different building, or other remote location from the patient allowing for remote surgical procedures.

Figure 3:
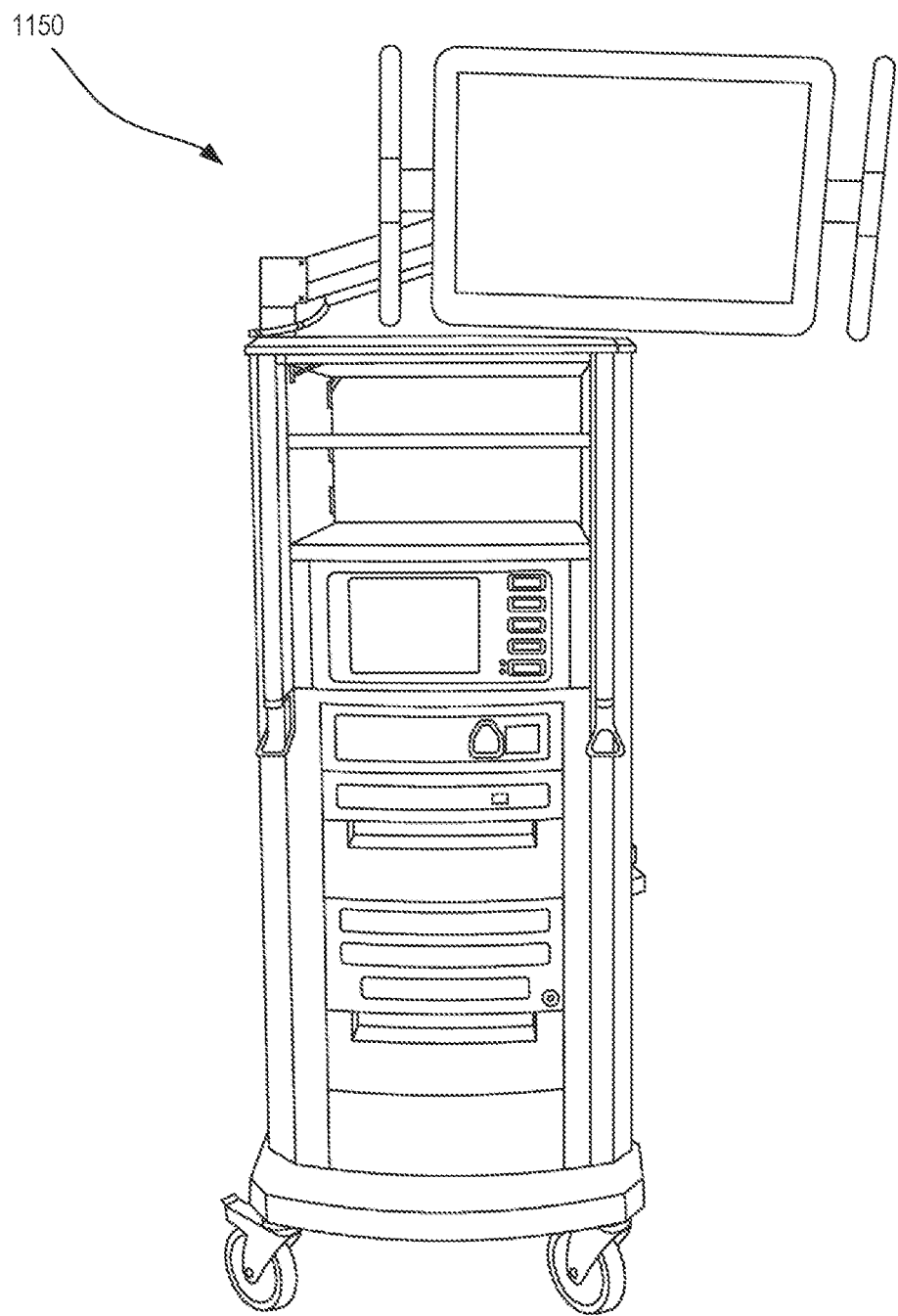
FIG. 3 is a perspective view of a user control console of the minimally invasive tele-operated surgery system shown in FIG. 1.

FIG. 3 is a perspective view of the auxiliary equipment unit 1150. The auxiliary equipment unit 1150 can be coupled with the endoscope (not shown) and can include one or more processors to process captured images for subsequent display, such as via the user control unit 1100, or on another suitable display located locally and/or remotely. For example, where a stereoscopic endoscope is used, the auxiliary equipment unit 1150 can process the captured images to present the surgeon S with coordinated stereo images of the surgical site via the left eye display 1112 and the right eye display 1114. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations.

Figure 4:
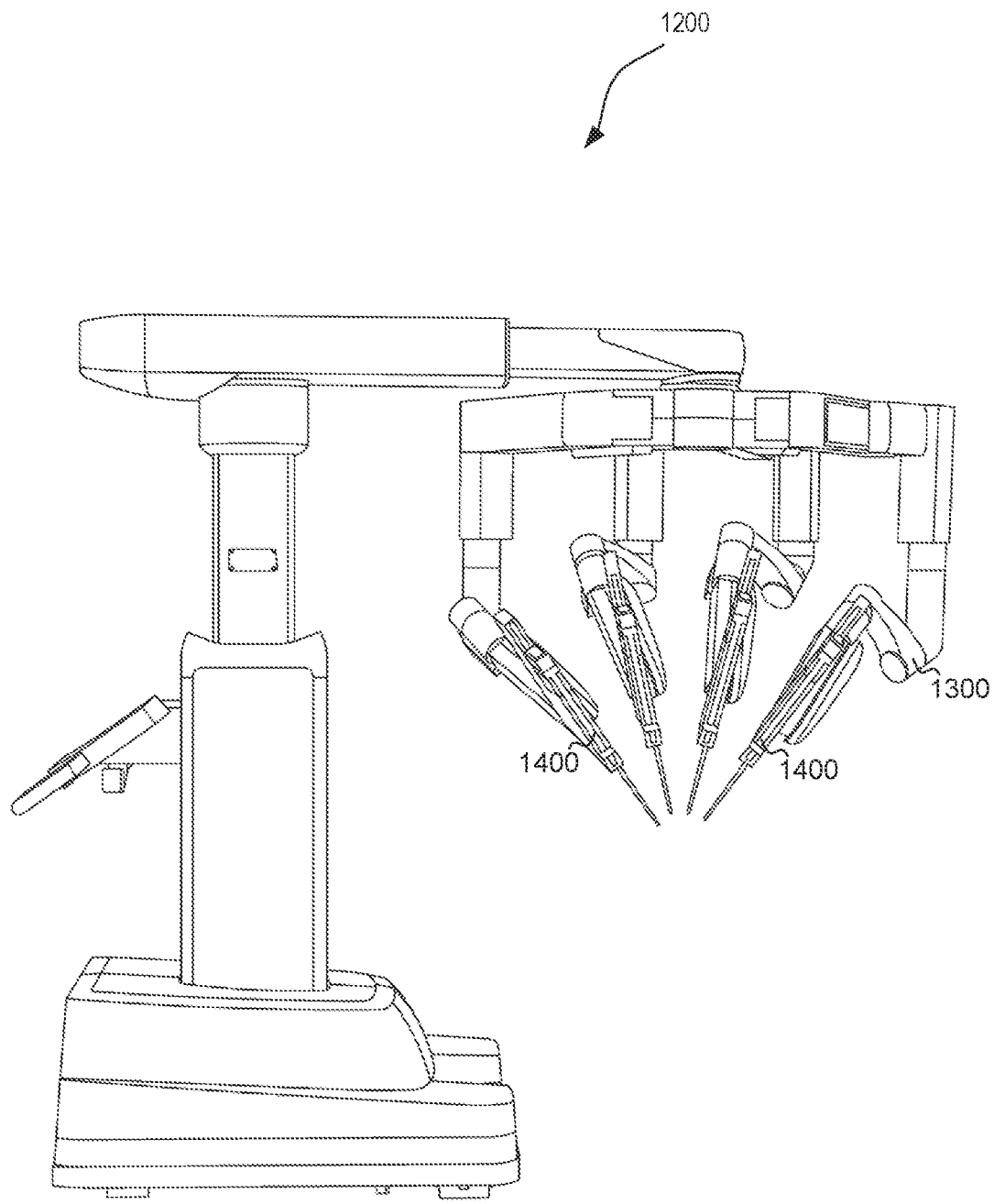
FIG. 4 is a front view of a manipulator unit, including a plurality of instruments, of the minimally invasive tele-operated surgery system shown in FIG. 1.

FIG. 4 shows a front perspective view of the manipulator unit 1200. The manipulator unit 1200 includes the components (e.g., arms, linkages, motors, sensors, and the like) to provide for the manipulation of the instruments 1400 and an imaging device (not shown), such as a stereoscopic endoscope, used for the capture of images of the site of the procedure. Specifically, the instruments 1400 and the imaging device can be manipulated by teleoperated mechanisms having a number of joints. Moreover, the instruments 1400 and the imaging device are positioned and manipulated through incisions or natural orifices in the patient P in a manner such that a kinematic remote center of motion is maintained at the incision or orifice. In this manner, the incision size can be minimized.

Many different clinical procedures can be performed via instruments 1400 operating through an incision or orifice in the patient P, which can interface with various objects while in the surgical environment within the patient including interfacing with tissue, organs, implants, surgical implements, as well as other instruments operating within the surgical environment. Many of these clinical procedures include using instruments to perform surgical retractor functions, such as moving, holding, lifting, retaining, or otherwise engaging tissue and organs. These instruments can include instruments designed to perform retractor functions, such as extendable surgical retractors and spreaders, as well as other non-retractor instruments that can nonetheless be manipulated to perform retractor functions, such as forceps-type instruments. Whether configured for performing surgical retractor functions or configured for other functions and capable of being used to perform retractor functions, an instrument capable of being used to perform retractor functions (also collectively called "retractor instrument") can often be unsuitable to perform particular retractor functions and clinical procedures.

Whether a retractor instrument is suitable for effectively engaging a target tissue and performing related retractor functions for a clinical procedure can be based on a variety of factors. These factors can include, for example, the types and fragility of tissues or organs involved in view of interface properties of the instrument, functional requirements for the procedure versus capabilities of the instrument, and the geometry of the surgical environment compared with manipulability of the instrument. As such, it can be beneficial for a clinician to be able to modify, adjust, and even customize interface characteristics of a retractor instrument 1400 for a particular procedure based on these factors. Accordingly, FIGS. 5A-5D are diagrammatic illustrations of various portions of a support apparatus 2800 configured to allow the clinician to modify interface characteristics of a retractor instrument 2400 according to suitability factors for the clinical procedure and the surgical environment when coupled with the instrument 2400. In particular, according to an embodiment, support apparatus 2800 is configured to be coupled to an instrument 2400 (which can be configured as or include a wrist assembly 2500) for performing surgical retractor functions during a clinical procedure, and for modifying characteristics in which the instrument 2400 interfaces or engages tissue or organs. In some embodiments, the support apparatus 2800 and the instrument 2400, or any of the components therein, are optionally parts of a surgical system that performs minimally invasive surgical procedures and that can include a manipulator unit, a series of kinematic linkages, a series of cannulas, or the like. The support apparatus 2800 and instrument 2400 (and any of the instruments described herein) can be used in any suitable surgical system, such as the MIRS system 1000 shown and described above and can be configured to perform multiple clinical retractor functions or interact with multiple objects.

Figure 5A:
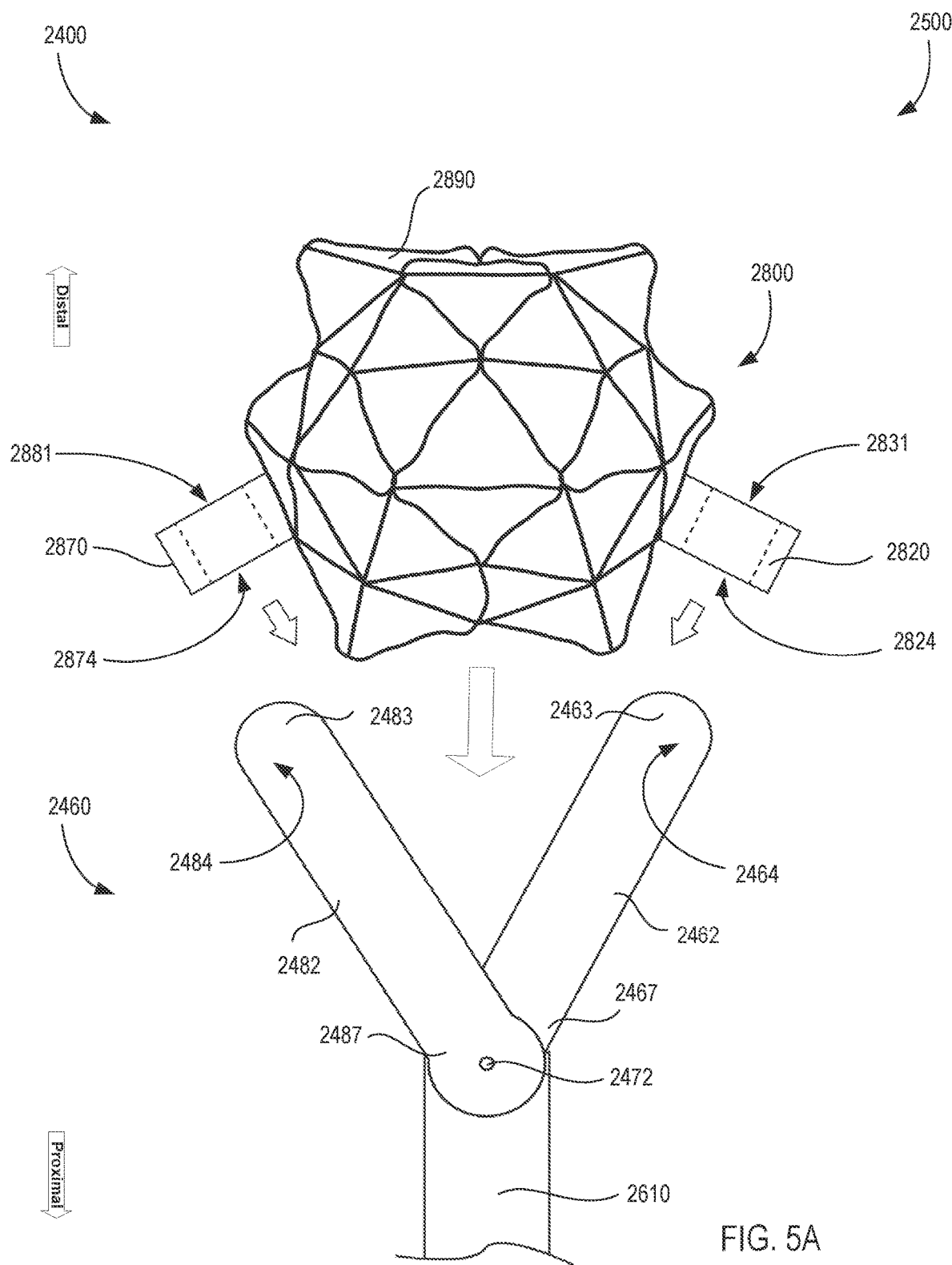
FIG. 5A is a diagrammatic front view of a removable support apparatus configured to be attached to an instrument of a surgery system, according to an embodiment, the support apparatus shown in a partially expanded configuration.
Figure 5B:
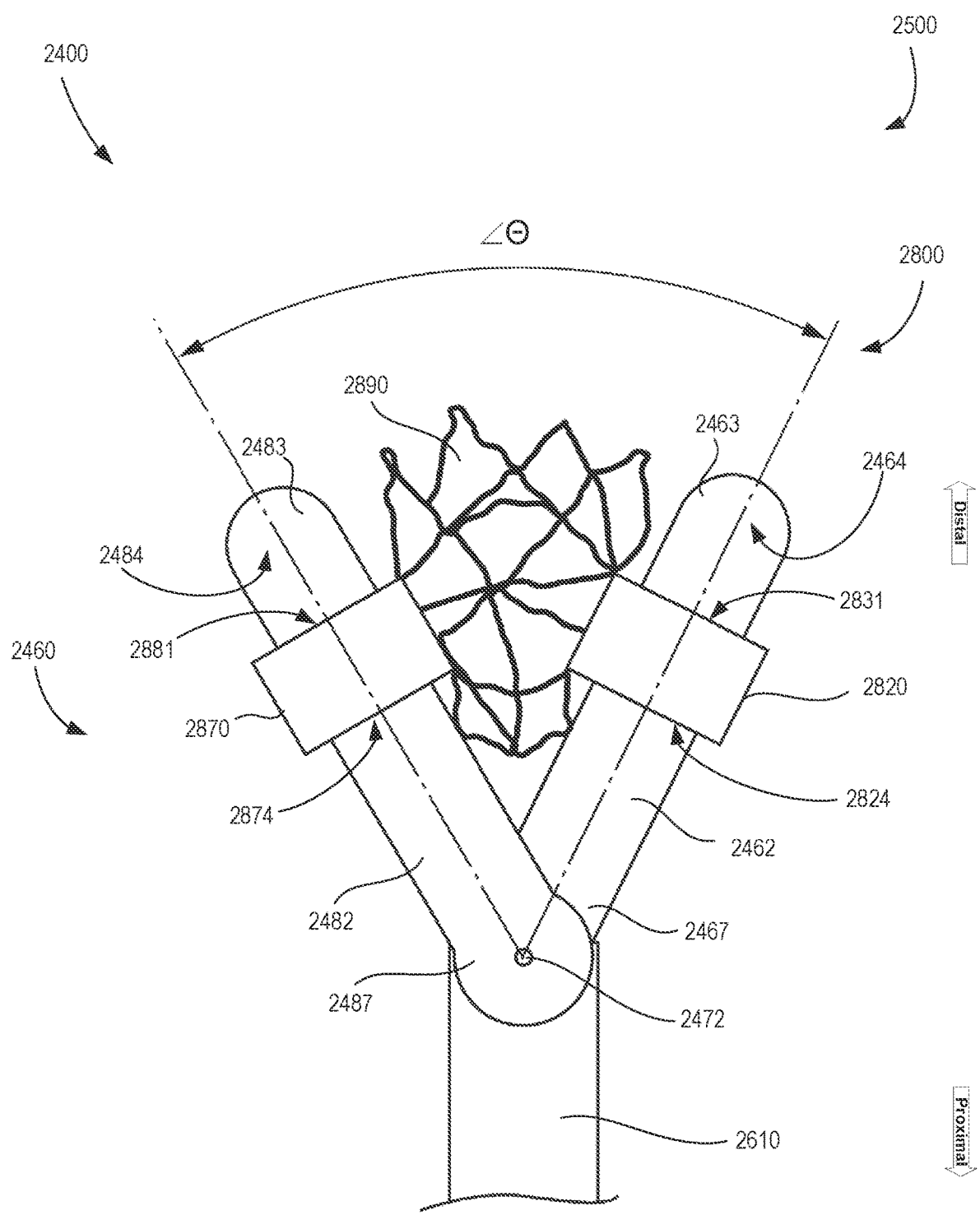
FIG. 5B is a diagrammatic front view of the removable support apparatus of FIG. 5A in an assembly with the instrument of a surgery system of FIG. 5A, with the removable support apparatus being coupled to the instrument.

FIG. 5A shows the support apparatus 2800 along with, but uncoupled from, the example instrument 2400. FIGS. 5B-5D show the support apparatus 2800 coupled to the instrument 2400. As discussed in greater detail below, when coupled with the instrument 2400, support apparatus 2800 can modify characteristics of the instrument that can affect, for example, aspects in which the instrument may interface or engage target tissue while performing clinical functions in the surgical environment. Referring to FIGS. 5A and 5B, the instrument 2400 to which the support apparatus is configured to be coupled can be any suitable instrument described herein or in copending U.S. Provisional Application No. 62/767,661, entitled "Medical Devices Having Multiple Blades and Methods of Use," filed Nov. 15, 2018, which is incorporated herein by reference in its entirety. Specifically, the instrument 2400 includes a clevis 2610, a first tool member 2462, and a second tool member 2482 (which together form an end effector 2460). The clevis 2610 can be a part of or coupled to one or more kinematic linkages of the MIRS system 1000 as described above. The first tool member 2462 has a proximal end portion 2467 that is movably coupled to the clevis 2610 and an opposite distal end portion 2463. Similarly, the second tool member 2482 has a proximal end portion 2487 movably coupled to the clevis 2610 and an opposite distal end portion 2483. The first and second tool members 2462 and 2482 are each rotatably coupled to the clevis 2610 such that the second tool member can be moved relative to the first tool member between the closed orientation (see e.g., FIG. 5C), and a second orientation (see e.g., FIG. 5B). In some embodiments, each of the proximal end portions 2467 and 2487 of the tool members can be rotatably coupled to the clevis 2610 via a pin 2472. As such, the second tool member 2482 can be rotated relative to the first tool member 2462 about the pin 2472 by an angle theta, $\angle \Theta$, shown in FIG. 5B for movement from the closed, first orientation shown in FIGS. 5C and 5D to the open, second orientation shown in FIG. 5B.

Although instrument 2400 is not limited to any particular type of instrument such as a surgical retractor, spreader, forceps, or gripping jaws, in some embodiments, the instrument 2400 can optionally be configured as a fan-blade type retractor instrument 2400. For example, in some embodiments, the first tool member 2462 can be a first retractor blade and the second tool member 2482 can be a second retractor blade. Thus, in some embodiments, the first retractor blade 2462 has a first tissue contact surface 2464 along a first side of the first retractor blade 2462. Similarly, the second retractor blade 2482 has a second tissue contact surface 2484 along a first side of the second retractor blade 2482. As discussed further below along with FIGS. 5B-5D, the support apparatus 2800 is configured to be coupled with the retractor instrument 2400 such that the support apparatus surrounds portions of the first and second tissue contact surface 2464, 2484 to modify interactions between the retractor instrument and target tissue via, for instance, the first and second tissue contact surfaces.

The first tool member 2462, and the second tool member 2482 can be moved by any suitable mechanism. For example, in some embodiments, the tool members can be moved by one or more tension members (e.g., cables, bands, or the like). For example, the first tool member 2462 is coupled to a first tension member (not shown), and the second tool member 2482 is coupled to a second tension member (not shown). In this manner, each of the tool members can be moved independently of the other tool members by actuation of the appropriate tension member. In other embodiments, any of the first tool member 2462, and the second tool member 2482 can be moved by a miniature motor, a hydraulic actuator, or the like.

Referring to FIG. 5C, when the second tool member 2482 (and therefore the instrument 2400) is in the closed orientation (also referred to herein as a closed, first orientation) each of the first and second tool members 2462 and 2482 are aligned with each other. As described in greater detail below along with FIG. 6, the closed orientation provides a compact orientation for installation and removal of the instrument 2400 combined with the support apparatus 2800 coupled thereto through a cannula 2314 for use within the surgical environment (not shown). In certain instances, when the instrument 2400 is in the compact closed orientation of FIG. 5C, the centerline of the instrument 2400 is aligned with the first and second tool members, and also oriented to be coaxial with a longitudinal axis (not shown) of an instrument shaft that controllably connects the instrument 2400 to a transmission assembly of a MIS surgical system as described above. After installation of the instrument 2400 into the surgical environment (not shown), the instrument 2400 can independently rotate the tool members 2462 and 2482 with respect to the clevis 2610 according to the surgical environment to perform clinical functions, which places the instrument 2400 in an extended second orientation (see e.g., FIG. 5B) that can have any number of orientations for the tool members.

Referring to FIG. 5A, the support apparatus 2800 includes a first sleeve 2820, a second sleeve 2870, and a flexible contact member 2890. The flexible contact member 2890 is coupled to each of the first sleeve 2820 and the second sleeve 2870, and is configured to be moved between a collapsed configuration and an expanded configuration when coupled to the instrument according to the orientation of the instrument 2400. The first sleeve 2820 is configured to be coupled to the first tool member 2462, and the second sleeve 2870 is configured to be coupled to the second tool member 2482. The flexible contact member 2890 is configured to be moved between a collapsed configuration when the second tool member 2482 is in the closed orientation (FIGS. 5C and 5D), and an expanded configuration when the second tool member is an open, second orientation (FIG. 5B).

Further, as shown in FIGS. 5B and 5C, in some embodiments the first sleeve 2820 is configured to be placed about a portion of the first tissue contact surface 2464 of the first retractor blade 2462. Likewise, the second sleeve 2870 is configured to be placed about a portion of the second tissue contact surface 2484 of the second retractor blade 2482. Referring to FIGS. 5C and 5D, in some embodiments, the first sleeve 2820 further defines a first pocket 2831 that is configured to receive the first retractor blade 2462 and to surround the portion of the first tissue contact surface 2464 about which the first sleeve is placed. The first sleeve 2820 also defines an opening 2824 into the pocket 2831 and as an entry through which the pocket 2831 can be accessed. Similarly, the second sleeve 2870 defines a second pocket 2881 that is configured to receive the second retractor blade 2482 and to surround the portion of the second tissue contact surface 2463 about which the second sleeve is placed. The second sleeve 2870 also defines an opening 2874 into the pocket 2881 and through which the pocket 2881 can be accessed. Thus, as shown in FIG. 5D, in some embodiments each of the first and second sleeves 2820 and 2870 surround the portion of the first and second retractor blades 2462 and 2482 about which they are placed when the support apparatus 2800 is coupled with the instrument 2400, and also surround a portion of the first and second tissue contact surface 2464, 2484 respectively. As described in greater detail below along with FIG. 6, such an embodiment can allow the support apparatus 2800 to be quickly and easily removably coupled to the instrument 2400 along with being securely coupled to the instrument 2400 during use. In addition, as described further below along with the flexible member 2890, the first and second sleeves 2820, 2870 modify interface characteristics of the instrument 2400 along with the flexible member 2890 based at least on the sleeves surrounding portions of the first and second tissue contact surfaces 2464, 2484 that are configured for engaging the tissue when the retractor tool 2400 performs retractor functions.

Referring to FIG. 5D, the flexible member 2890 is configured to move to a collapsed configuration when the support apparatus 2800 is coupled to the instrument and the instrument is in the closed orientation. As such, the flexible member 2890 is configured to have sufficient flexibility so that it can bend, fold, roll and otherwise collapse into a compact collapsed configuration that can fit within spaces between the first and second sleeves 2820, 2870 and retractor blades 2462, 2482 and/or roll, fold or otherwise move close to the sleeves to which the flexible member is coupled. Further, as discussed below along with FIG. 6, the flexible member 2890 is also configured with sufficient flexibility to collapse, fold or flex as needed when being advanced through the cannula 2314 (see e.g., FIG. 5C). In addition, along with flexibility and compactness characteristics, the flexible member 2890 is configured to be resilient and have sufficient strength for engaging tissue and effectively performing retractor functions without failing.

The flexible member 2890 can be formed from various materials having appropriate characteristics described herein, and can have various arrangements, designs and configurations. Flexible member 2890 can be formed from an appropriate flexible member and be coupled to and flexibly extend between each of the connection members in many different arrangements, such as formed being formed from a mesh material having various fibrous connections as shown in FIGS. 5A-5D. In other embodiments shown herein, the flexible member is formed from other materials having various connection designs and configurations. It is understood that these are example flexible member designs and that many different options can be included with respect, for instance, to designs, arrangements, configurations, materials, connections and shapes of the flexible member. For instance, the flexible member 2890 could be formed from a sheet material; an elastomeric material that has been shaped, extruded or molded into a desired arrangement; a plurality of interwoven fibers, strands or other elongate members coupled to each other; a matrix, spider web or other arrangement of interconnecting members; a fabric material; etc. It is understood that many different arrangements, designs, materials, and configurations for the flexible member can provide various characteristics for the support apparatus and for modifying tissue interface characteristics of the instrument as appropriate for the surgical environment and clinical functions.

Figure 6:
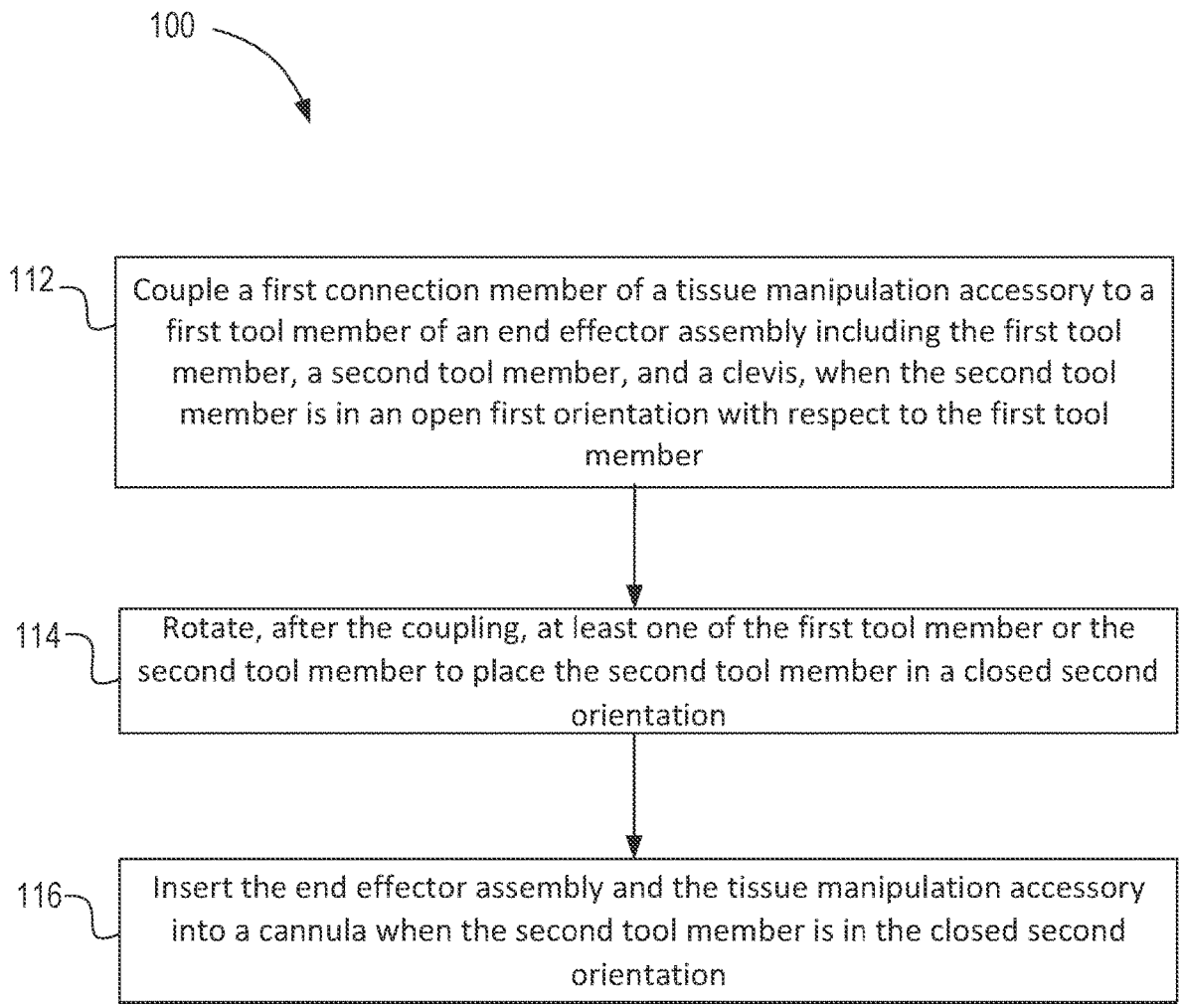
FIG. 6 illustrates a method for assembling a removable support apparatus with an instrument of a surgery system and using the assembly in a surgical environment, according to an embodiment.

The support apparatus 2800 (and any of the support apparatus described herein) can be used in any suitable surgical method. For example, in some embodiments, the support apparatus 2800 can be included in a surgical kit that includes, among other items, an instrument (e.g., the instrument 2400). The support apparatus 2800 can be detached from the instrument, and in use, a practitioner can either perform a procedure using only the instrument or, alternatively, can couple the support apparatus 2800 to the instrument to perform a procedure. This arrangement provides additional flexibility for the practitioner to select the configuration that is best suited for the desired procedure. As an example, FIG. 6 is flow chart method 100 of using a support apparatus, according to an embodiment. Although the method 100 is described along with FIGS. 5A-5D as being performed with the support apparatus 2800, in other embodiments, the method 100 (and any of the methods described herein) can be performed using any of the devices described herein. Referring to FIG. 5A along with FIG. 6, the method 100 includes coupling, at 112, a first connection member 2820 of a tissue manipulation accessory 2800 to a first tool member 2462 of an end effector assembly 2460 that includes the first tool member 2462, the second tool member 2482 and the clevis 2610. Referring to FIG. 5A, the coupling 112 is performed when the second tool member 2482 is in an open, first orientation with respect to the first tool member, such as the open orientation shown in FIG. 5A. In comparison with the closed orientation shown in FIG. 5C, an open orientation allows easy access for the user to couple the first connection member 2820 to the first tool member 2462.

In the example shown in FIGS. 5A-5D, coupling the first connection member 2820 to the first tool member 2462 can include sliding the first sleeve 2820 over the first retractor blade 2462 such that the first retractor blade 2462 enters the opening 2824 into the first pocket 2831 and extends through the first pocket 2831 as shown in FIGS. 5C and 5D. In the example shown in FIGS. 5A-5D, the second connection member 2870 or second sleeve 2870 can be coupled to the second tool member 2482 or second retractor blade 2482 tool member prior to, after, or simultaneously with coupling (at 112) the first connection member 2820 in a similar manner via the opening 2874 into the second pocket 2881. However, a particular order for coupling the connection members can be helpful for other embodiments, such as discussed below along with FIG. 7A. It can be helpful to couple the first connection member 2820 when the second tool member 2482 is in the open orientation, and in which the first and second connection members are apart from each other, so that the flexible member expands and extends between the connection members without binding or being otherwise improperly arranged and potentially impairing functionality in the surgical environment. Although the coupling is shown as being performed while in an open orientation, the open orientation can be any sufficiently open orientation between the tool members. Similarly stated, the coupling can be performed when the second tool member is an any suitable orientation, include a partially-opened orientation.

Referring to FIGS. 5B-5D and 6, the method 100 further includes rotating, at 114 and after the coupling 112, at least one of the first tool member 2462 and the second tool member 2482 to place the second tool member 2482 in the closed, second orientation. Performing coupling while the tool members are in an open orientation, along with performing rotating (at 114) after the coupling, can help ensure that the flexible member 2890 is reversibly collapsed when it moves into the closed, second orientation, which can further avoid potential challenges during use of the support apparatus 2800 while in the surgical environment. As shown in FIG. 5B, when in the open, first orientation, the flexible member 2890 extends from its coupling to the first connection member 2820 to its coupling to the second connection member 2870 between the first and second tool members. FIGS. 5C and 5D illustrate how the flexible member 2890 can collapse between the first and second tool members and first and second connection members when the tool members move to be in the second, closed orientation, which can include folded, wrapped, and placed in various other types of collapsed arrangements. In some embodiments, the flexible member 2890 can include a crease, pre-determined folds or accordions (not shown), or other features that can help guide the collapsed arrangement of the flexible member.

Referring to FIG. 5C and FIG. 6, the method 100 additionally includes inserting, at 116, the end effector assembly 2400 and the tissue manipulation accessory 2800 into the cannula 2314 when the second tool member is in the closed second orientation. FIG. 5C shows a portion of a cannula 2314 through which the assembly is inserted for installation into the surgical environment. The method 100 can further include introducing (not shown), after the inserting, the end effector assembly 2400 and the tissue manipulation accessory 2800 into a body cavity (not shown), to which the cannula 2314 leads as the assembly is advanced through the cannula into the surgical environment (not shown). After the end effector assembly 2400 and tissue manipulation accessory 2800 are inserted into the body cavity (not shown), the method 100 can also include rotating (not shown) at least one of the first or the second tool members 2462, 2482 from the closed orientation towards an open orientation to perform clinical functions.

Although method 100 is described above using the example end effector assembly or instrument 2400 and the support apparatus 2800, it is understood that the method 100 can be performed along with various types and configurations of instruments having a first and second tool member movably coupled to a clevis. In addition, method 100 can be performed various configurations and options for the support apparatus including configurations having different types of flexible members and different options for coupling the first and second connection members to the first and second tool members. For example, FIGS. 7A-7D shows a support apparatus 3800 having different coupling mechanisms and illustrating another option, as an example, for the flexible contact member.

Figure 7A:
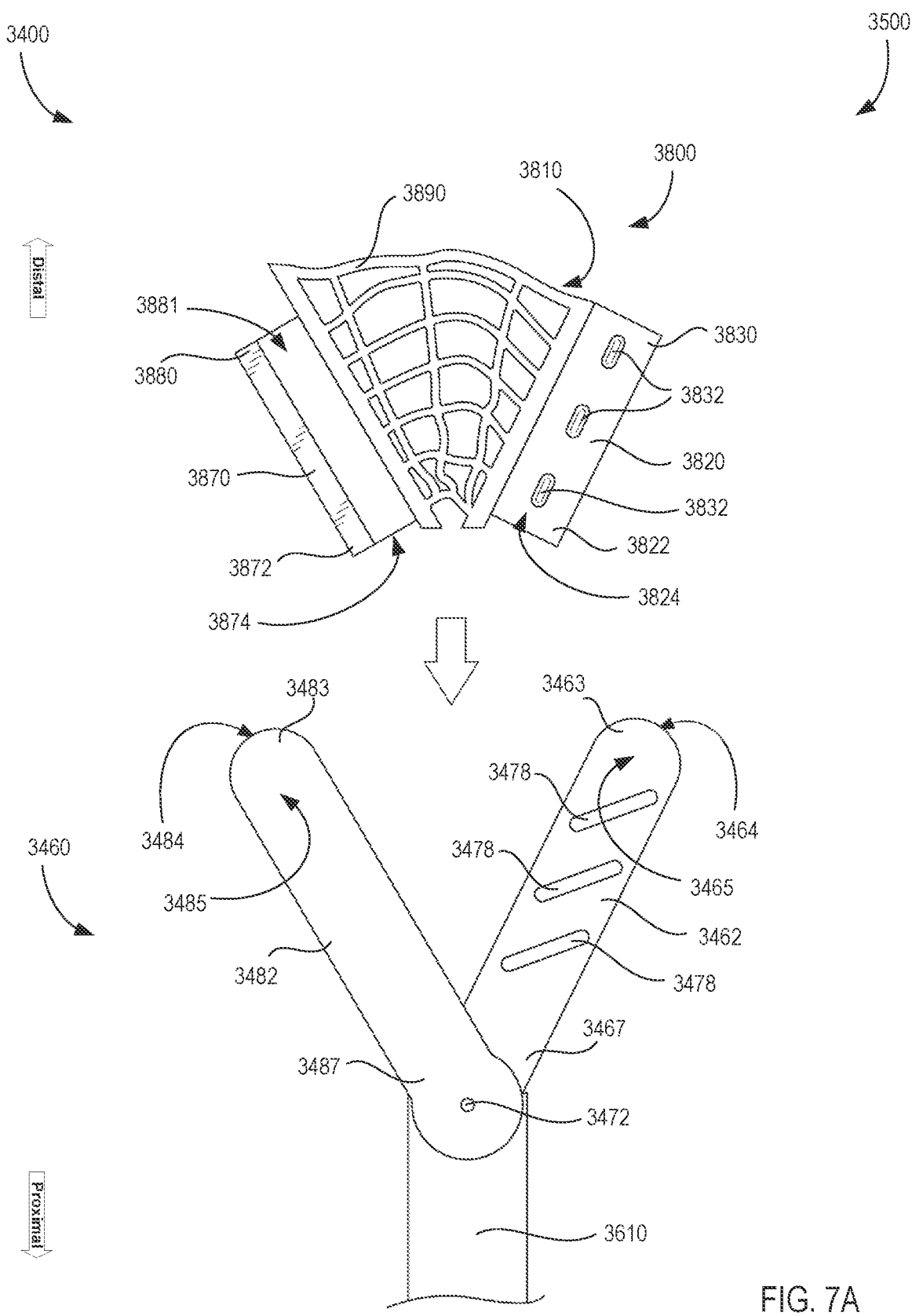
FIG. 7A is a diagrammatic front view of a removable support apparatus configured to be attached to an instrument of a surgery system as indicated by Arrow BB along with a portion of the instrument, according to an embodiment, which are shown in a first orientation.
Figure 7B:
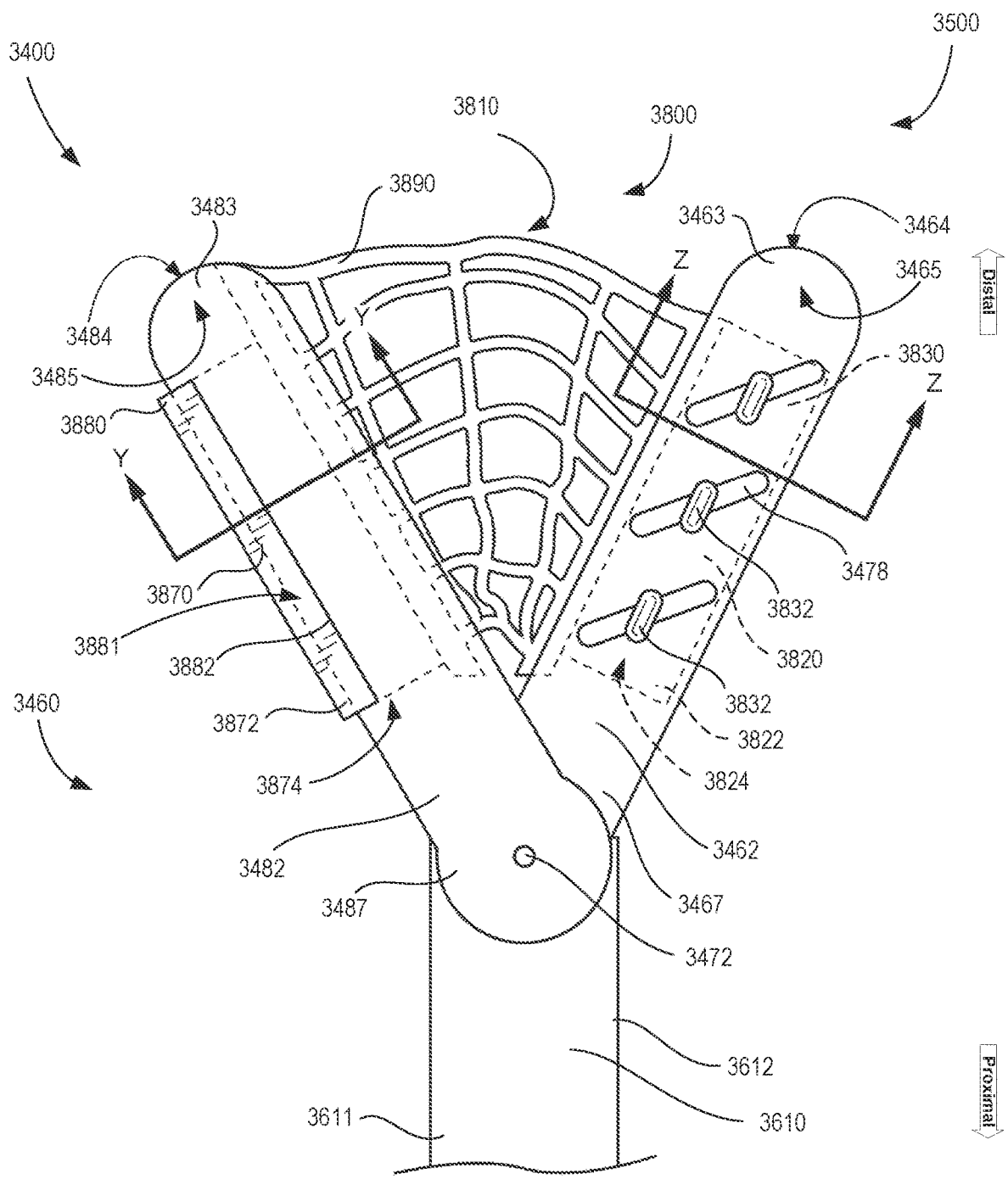
FIG. 7B is a diagrammatic front view of the removable support apparatus of FIG. 7A in an assembly with the instrument of a surgery system of FIG. 7A, which are shown in a second orientation.
Figure 7C:
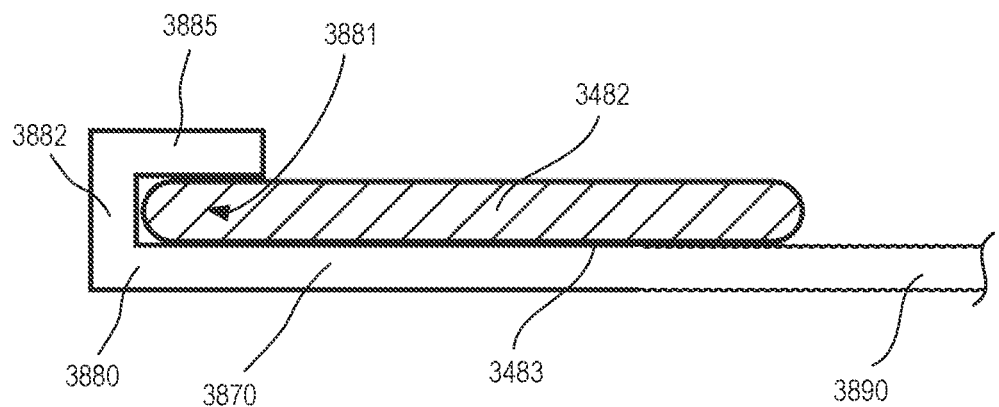
FIGS. 7C and 7D are cross-sectional views of portions of the removable support apparatus assembly shown in FIG. 7B, as viewed from lines Y-Y and Z-Z respectively shown in FIG. 7B.
Figure 7D:
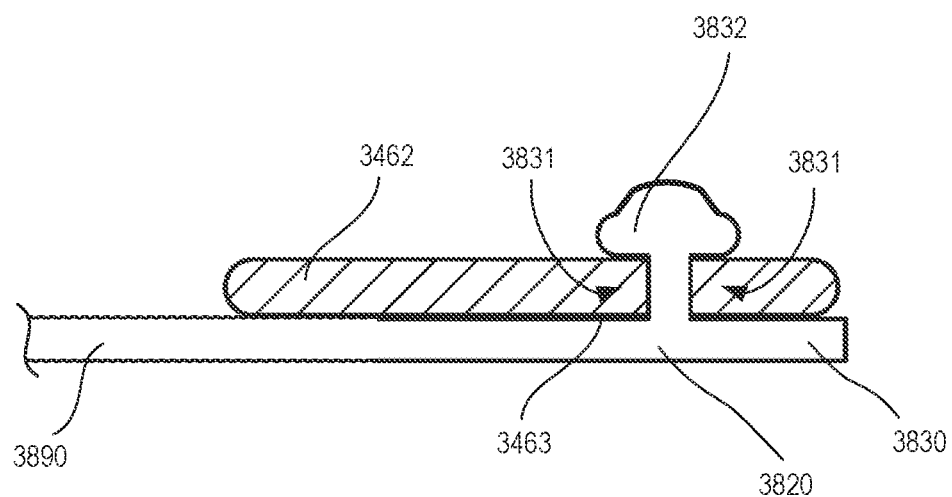

FIGS. 7A-7D show a tissue manipulation accessory 3800 configured to be coupled to an instrument 3400 shown as uncoupled from the instrument 3400 (FIG. 7A), as well as coupled with the instrument (FIGS. 7B-7D). Similar to support apparatus 2800, when coupled with the instrument 3400, tissue manipulation accessory 3800 can modify characteristics of the instrument that affect, for example, aspects in which the instrument interfaces or engages target tissue during use while performing clinical functions. Further, tissue manipulation accessory 3800 and instrument 3400 both generally include the same aspects and features as described above along with support accessory 2800 and instrument 2400 except as discussed herein.

Referring to FIGS. 7A and 7B, the instrument 3400 to which the support apparatus is configured to be coupled includes a clevis 3610, a first tool member 3462, and a second tool member 3482. The clevis 2610 can be one or more kinematic linkages of an MIRS system 1000 as described above. The first tool member 3462 has a proximal end portion 3467 that is movably coupled to the clevis 3610 and an opposite distal end portion 3463. Similarly, the second tool member 3482 has a proximal end portion 3487 movably coupled to the clevis 3610 and an opposite distal end portion 3483. The first and second tool members 3462 and 3482 are each rotatably coupled to the clevis 3610 such that the second tool member can be moved relative to the first tool member between the closed orientation (not shown), and a second orientation (see e.g., FIG. 7B).

Like instrument 2400 and support apparatus 2800, the instrument 3400 with which the support apparatus 3800 can be coupled is not limited to any particular type of instrument. Support apparatus 3800 can be configured to be coupled with various types of instruments such that it can provide benefits pertaining to modifying tissue interactions for the instrument, such as for example, a surgical retractor, a spreader, forceps, and set of gripping jaws. For illustration purposes of various aspects and features of the support apparatus 3800 when coupled with an instrument 3400 including for discussing potential benefits with respect to retractor functions, the instrument 3400 is configured as a retractor instrument 3400 in FIGS. 7A-7D. As such, the first tool member 3462 can be a first retractor blade 3462 and the second tool member 3482 can be a second retractor blade 3482. The first retractor blade 3462 has a first tissue contact surface 3464 along a first side of the first retractor blade, and a third tissue contact surface 3465 along a second side of the first retractor blade. Similarly, the second retractor blade 3482 has a second tissue contact surface 3484 along a first side of the second retractor blade and a fourth tissue contact surface 3485 along a second side of the second retractor blade. (See FIGS. 7A and 7B, which show the first and second tissue contact surfaces oriented away from the viewer, as opposed to being oriented toward the viewer in FIGS. 5A-5D). The first and second tissue contact surfaces 3464, 3484 on the first side of each of the first and second retractor blades 3462, 3482 are configured as the primary tissue contact surfaces for the retractor instrument 3400.

As further shown in FIGS. 7A and 7B, the first retractor blade 3462 includes a plurality of fenestrations 3478 formed therethrough along the length of the first retractor blade 3462. The fenestrations 3478 are configured as angled slots through the first retractor blade 3462. However, it is understood that the fenestrations can be formed through more than one retractor blade including the second retractor blade 3482, and can include openings through the blades have a wide variety of shapes, patterns, numbers, spacings and arrangements formed through the blades. The fenestrations can be formed in the retractor blades to modify the blade's purchase with target tissue when performing clinical functions. Further, as discussed further below, features of the support apparatus 3800 can take advantage of retractor blade fenestrations for coupling with the blade.

The instrument 3400 generally includes the same movement characteristics as instrument 2400 discussed above along with FIGS. 5A-5D, such that the retractor blades 3462 and 3482 can rotate with respect to the clevis 3610 and can have similar ranges of motion between closed orientation and open orientations. Likewise, the first tool member 3462, and the second tool member 3482 can be moved by any suitable mechanism. For example, in some embodiments, the tool members can be moved by one or more tension members (e.g., cables, bands, or the like). For example, the first tool member 3462 is coupled to a first tension member (not shown), and the second tool member 3482 is coupled to a second tension member (not shown). In this manner, each of the tool members can be moved independently of the other tool members by actuation of the appropriate tension member. In other embodiments, any of the first tool member 3462, and the second tool member 3482 can be moved by a miniature motor, a hydraulic actuator, or the like.

Referring to FIGS. 7A and 7B, the tissue manipulation accessory 3800 includes a first removable connector 3820, a second removable connector 3870, and a flexible contact member 3890. The flexible contact member is coupled to each of the first removable connector and the second removable connector and is configured to be moved between a collapsed configuration and an expanded configuration when coupled to the instrument according to the orientation of the instrument 3400. The first removable connector 3820 is configured to be coupled to the first tool member 3462, and the second removable connector 3870 is configured to be coupled to the second tool member 3482. The flexible contact member 3890 is configured to be moved between a collapsed configuration when the second tool member 3482 is in the closed orientation (not shown), and an expanded configuration when the second tool member is an open, second orientation (FIG. 7B). As shown in FIG. 7B, the first removable connector 3820 is configured to be placed about a portion of the first tissue contact surface 3464 of the first retractor blade 3462. Likewise, the second removable connector 3870 is configured to be placed about a portion of the first tissue contact surface 3484 of the second retractor blade 3482.

Referring to FIGS. 7B and 7D, the first removable connector 3820 includes a plurality of retention members 3832 configured to attach the connector to the first retractor blade 3462 for use during clinical functions. The retention members 3832 are further configured to retain the coupled arrangement between the first removable connector 3820 and the first retractor blade 3462 during use including when installing and withdrawing the assembly into and from the surgical environment, such as through a cannula, as well as when interacting with tissue. The plurality of retention members 3832 are configured as cleat-shaped protrusions 3832 that can securely engage the angled, slotted fenestrations 3478 in the first retractor blade 3462 to attach the first removable connector 3820 to the first retractor blade via a firm, yet removable connection. Although three retention members 3832 are shown in FIG. 7B that engage three respective angled, slotted fenestrations 3478, fewer retention members can provide sufficient attachment and retention capabilities in many embodiments and for many intended usages, and a greater number of retention members can be appropriate for other embodiments and for different intended usages, such as being coupled to a surgical retractor designed for encountering high tissue engagement forces and stresses.

Referring to FIG. 7D, each of the retention members 3832 defines a first pocket 3831 between an inner side of the cleat-shaped protrusion and a corresponding portion of the removable connector 3820. The first pocket 3831 is configured to receive a portion of the first retractor blade 3462 therein and to extend around a portion of the first tissue contact surface 3464. As shown in FIG. 7B along with FIG. 7D, each of the retention members 3832 are configured to have elongate shaped distal end portions or heads that can resemble a deck cleat for a boat, which can each fit through a corresponding one of the fenestration slots 3478 in the first retractor blade 3462 during installation by aligning each of the elongate shaped heads with the corresponding slot 3478. After attaching the first removable connector 3820 to the first retractor blade 3462, the first removable connector 3820 can be rotated to the installed position shown in FIG. 7B to lock the connector/blade coupled connection in place and retain the coupled connection as an assembly during use. In this manner, each of the retention members 3832 can easily be attached to the first retractor blade 3462 to retain the first removable connector 3820 when rotated with respect to the corresponding angled slots 3478 during clinical use of the coupled connections in the configuration shown in FIG. 7B.

In addition, as shown in FIGS. 7B and 7C, the second removable connector 3870 defines a second pocket 3881 that is configured to receive the second retractor blade 3482 and to surround the portion of the second tissue contact surface 3463 about which the second sleeve is placed. The second removable connector 3870 also defines a pocket 3881 for receiving the second retractor blade and an opening 3874 through which the pocket 3881 can be accessed. The second removable connector 3870 includes a second retention member 3882 configured as a lateral hook-shaped protrusion 3885. The retention member 3882 defines the pocket 3881 between an inner side of the hook-shaped protrusion 3885 and a corresponding portion of the removable connector 3870. The pocket 3881 is configured to receive a portion of the second retractor blade 3482 therein and to extend around a portion of the second tissue contact surface 3484. The pocket 3881 is configured to retain the second removable connector 3870 on the second retractor blade 3482. The retention member 3882 is configured further to maintain attachment between the second removable connector 3870 and the second retractor blade 3482 during use including when installing and withdrawing the coupled blade/support apparatus assembly into and out from the surgical environment such as through a cannula, and when interacting with tissue. The second retention member 3882 can securely engage the outer, lateral edge portion of the second retractor blade 3482 to attach the second removable connector 3870 to the second retractor blade 3482 via a firm, yet selectively removable connection. The second retention member 3882 can be shaped and sized to form an interference fit when attached to the outer edge portion of the second retractor blade 3482 to maintain a clamping force with the outer edge portion of the second retractor blade 3482 to retain the coupled attachment during use. After attachment of the first removable connector 3820 to the first retractor blade 3462 along with attachment of the second removable connector 3870 to the second retractor blade 3482, the support apparatus 3800 is securely, yet removably, attached to the instrument 3400.

The secure coupling between the support apparatus 3800 and the first and second retractor blades is maintained during clinical usage of the coupled assembly based on cooperation of the first and second removable connectors 3820, 3870. As discussed above, the first removable connector 3820 can attach and retain the first removable connector 3820 to the first retractor blade 3462 via a plurality of retention members 3432 that securely engage the fenestrations 3478. In this manner, the attachment of the first removable connector 3820 to the first retractor blade 3462 is retained while the instrument/support apparatus assembly encounters forces generally aligned lengthwise with the first retractor blade 3462 between the proximal end 3467 and distal end portion 3463 and parallel to the first tissue contact surface 3464 of the first retractor blade (i.e., in fore-aft directions along the first side of the blade), as well as forces oriented in a normal direction to the blade and also parallel to the first tissue contact surface (i.e., in lateral directions along the first side of the blade including lateral rotation directions when the blades are retracting/extending). Stated differently, the first retention members 3832 securely retain the first removable connector 3820 to the first retractor blade 3462 despite the application of forces applied to the coupled assembly being applied from many directions as long as the plurality of retention members 3432 are not rotated into alignment with the fenestration slots 3478. When the first retention members are oriented out of alignment with the fenestration slots 3478 as shown in FIG. 7B, the first retention members 3432 act like cleats to lock the first removable connector 3820 in the coupled attachment with the first retractor blade 3462, and to retain the coupled attachment during use. In this manner, each of the retention members 3832 can easily be attached to the first retractor blade 3462 to retain the first removable connectors 3820 when rotated with respect to the corresponding angled fenestration slots 3478 during use in the attached configuration shown in FIG. 7B.

Further, the second retention member 3882 cooperates with the plurality of first retention members 3432 to enhance overall retention of the support apparatus 3800 to the retractor instrument 3400 as described further below, which includes preventing the first removable connector 3820 from rotating such that the first retention members 3432 can align with the fenestration slots 3478. As shown in FIG. 7C, the second connector 3870 defines the pocket 3881 that is configured to receive the second retractor blade 3482 and to surround the portion of the second tissue contact surface 3465 about which the second sleeve is placed. In addition, the shape of the clip 3885 and its attachment to the outer lateral edge portion of the second retractor blade 3482 maintains the rotation orientation of the support apparatus 3800 when in the attached arrangement shown in FIG. 7B, which prevents the first retention members 3432 from being rotated in a manner that can permit detachment. Further, the force-fit clamping connection of the second retention member 3882 and clip 3885 along the edge portion of the second retractor blade 3482 acts to securely retain the second removable connector 3870 in its coupled attachment to the second retractor blade 3462 despite applied forces in almost all directions that could occur during use.

The coupled attachment of the second removable connector 3870 is further reinforced against forces that could be applied in the lateral, rotary outward direction in which the second retractor blade 3482 rotates when the retractor instrument extends outward (i.e., in the direction of angle theta away from the first retractor blade that is shown in FIG. 5B), which could apply forces to the retention member 3882 in a removal direction for unhooking the clip 3885 from the second retractor blade 3482. In particular, the hook shape of the retention member 3882 is configured to be opposite from the flexible contact member 3890 that extends between the first and second removable connector members 3832, 3882 during use, such that clip 3885 is oriented toward the flexible contact member 3890. This arrangement allows the flexible contact member 3890 to counteract any such forces being applied to the second retention member 3882 during usage when the flexible contact member 3890 is extended and the support apparatus 3800 is in an open orientation. When the retractor blades 3462, 3482, are rotated apart in an open orientation such as shown in FIG. 7B for performing retractor clinical functions, the extended flexible contact member 3890 applies connection forces between the removable connector members 3820, 3870, and to the second retention member 3882, in an inward rotation direction that opposes any applied forces in a direction that could unhook the clip 3885 of the second retention member.

As such, the first and second removable connectors 3420, 3470 can be securely attached and retained to the first and second retractor blades 3462, 3482 during usage of the support apparatus 3800 when in a coupled assembly condition with the retractor instrument 3400, as well as be easily attached and removed as desired. Further, as shown in FIG. 7B and discussed above, the first and second removable connectors 3820, 3870 are configured to surround a portion of the corresponding retractor blade 3462, 3482 including at the first tissue contact surface 3464 and the second tissue contact surface 3484 disposed on a first side of the first and second retractor blades 3462, 3482. Thus, the flexible contact member 3890 can be attached to the first removable connector 3820 at a region that covers a portion of the first tissue contact surface 3464 of the first retractor blade 3462, and to the second removable contactor 3470 at a region that covers the second tissue contact surface 3484, such that a first contact surface 3494 of the flexible contact member 3490 cooperates with the first and second removable connectors along a first outer side 3810 of the support apparatus to modify engagement of the retractor tool 3400 with target tissue.

Stated differently, as shown in FIGS. 7A and 7B, a first outer side 3810 of the support apparatus 3800 is configured to be disposed between the first and second tissue contact surfaces 3464, 3484 of the retractor tool 3400 and target tissue during usage, which modifies the engagement of the retractor tool 3400. The first outer side 3810 includes a first contact surface 3494 of the flexible contact member and outer surfaces of the first and second removable connectors 3820, 3870 that cover the first and second tissue contact surfaces 3464, 3484. The flexible member 3890 is configured to move to a collapsed configuration when the tissue manipulation accessory 3800 is coupled to the instrument and the instrument is in the closed orientation. As such, similar to flexible member 2890, the flexible member 3890 is configured to have sufficient flexibility so that it can bend, fold, roll and otherwise collapse into a compact collapsed configuration that can fit within spaces between the first and second removable connectors 3820, 3870 and retractor blades 3462, 3482 and/or roll, fold or otherwise move close to the sleeves to which the flexible member is coupled. Further, as discussed above along with FIG. 6, the flexible member 3890 is configured with sufficient flexibility to collapse, fold or flex as needed when being advanced through a cannula (not shown; see e.g., FIG. 5C).

As described along with other embodiments below and along with embodiment 2800 above, the flexible member can be configured and formed from various materials and arrangements, which can provide various characteristics for the tissue manipulation accessory as appropriate for the surgical environment and clinical functions. As shown in FIGS. 7A and 7B, the flexible member 3890 is configured to have a spider-web type pattern extending radially outward from the clevis 3610 in the region between the first retractor blade 3462 and the second retractor blade 3482. As such, the flexible contact member 3890 includes a series of elongate lateral rings extending from the first retractor blade 3462 to the second retractor blade 3482, as well as a series of elongate radial supports extending distally outward from a central portion near the clevis 3610 and connecting the lateral rings.

Thus, the flexible contact member 3890 forms an interconnected support web between the first and second retractor blades 3462, 3482, which can interface with tissue and organs when performing retractor function to modify the contact as desired. For instance, flexible contact member 3890 can increase the area of retractor contact with the tissue during use of the support apparatus 3800 when coupled to the instrument 3400, by extending between the retractor blades 3462, 3482 and interfacing with tissue between the blades during retractor functions. Further, the flexible contact member 3890 can enhance the retractor contact with tissue during clinical functions versus the contact provided by the instrument 3400 alone, such as by spreading contact forces along the increased contact area, which can avoid tissue damage from applying concentrated forces with the first and second retractor blades alone.

It is understood that other modifications and benefits can be provided via the coupled attachment of the support apparatus 3800 to the retractor instrument 3400. In addition, in other embodiments, a support apparatus according to aspects described herein can have a wide variety of options for customized configurations, features and combinations of features that can provide various benefits and further modify tissue interfaces. Such wide varieties of options can be based, for example, on the type of instrument and features of the instrument(s) for their intended attachment, the intended clinical usage including tissue characteristics and their interactions with the same, appropriate retention strength for the clinical functions, and desired tissue purchase for the clinical functions. Further, it is understood that the same support apparatus can be configured to be coupled with many different types of instruments such that the support apparatus can be configured to modify tissue interactions of those instruments in a universally beneficial manner, such as to enhance the instrument's ability to push, move or retain tissue effectively.

In addition, it is understood that a support apparatus described herein can include various customized configurations, features and combinations of the same, and also include generally universally configurations, features and combinations of the same that can provide benefits when the support apparatus is coupled when different types of instruments. As an example, FIGS. 8A, 9-12, 14A-16 and 18 show various views of a support apparatus 4800, according to an embodiment, having different and varied aspects, characteristics, and features compared with support apparatus 2800 and 3800 discussed above, which can be beneficial for use with many different types of instruments, and which can provide particular benefits when the support apparatus is coupled with an expandable retractor-type instrument, such as instrument 4400 shown in FIGS. 8A-13 and 15-18 according to an embodiment. The instrument 4400 (and any of the instruments described herein) can be used in any suitable surgical system, such as the MIRS system 1000 shown and described above.

Referring to FIGS. 8A-13 and 15-18, the instrument 4400 includes a transmission assembly 4700 (that can function as an actuator mechanism or transmission mechanism), an instrument shaft 4410, a wrist assembly 4500, and an end effector 4460. As with instruments 2400 and 3400, instrument 4400 includes one or more tension members that have largely been omitted in FIGS. 8A-13 and 15-18 to show more clearly various features pertaining to the support apparatus 4800 and the rotatable tool members of the end effector 4460, as well as pertaining to controlling operations of the three tool members to perform various combinations of clinical functions without switching instruments. However, for clarity purposes, portions of some of the corresponding tension member for the respective tool members discussed hereafter are shown in FIGS. 8B, 9 and 11-13 to illustrate related features discussed herein, such as operability of one or more of the tool members for various clinical and medical functions and independent control of each of the tool members. Further, the illustrated portions of the tension members show some of the respective routing of the tension members through the instrument 4400 along with coupling of each tension member with the respective tool member.

Although referred to herein as tension members or cables, it is understood that various other types of drive components, members, or mechanisms, and/or actuation components, members, or mechanisms can be arranged to implement force-transmitting and orientation-controlling actions with respect to components of instrument 4400 including with respect to its tool members. These features can further cooperate with one or more additional drive mechanisms to implement these actions with respect to the instrument 4400, such as having force applied to components of the instrument via the transmission 4700, or such components being actuated or driven via the transmission 4700, in order to implement desired effects for each of the tool members and perform various clinical and medical functions.

Referring to FIGS. 8A-9 and 11-13, the instrument 4400 includes a first tension member 4420 (which functions as an actuation member), and a second tension member 4430 (which functions as an actuation member) that couple the transmission 4700 to the wrist assembly 4500. Specifically, the first tension member 4420 is coupled to the first proximal end portion 4467 of the first tool member 4462 and the second tension member 4430 is coupled to the second proximal end portion 4487 of the second tool member 4482. The instrument 4400 is configured such that movement of the tension members can produce rotation of the wrist assembly 4500 (i.e., pitch rotation) about a first axis of rotation, $A_1$, yaw rotation of the end effector 4460 about a second axis of rotation, $A_2$, grip rotation of the tool members of the end effector 4460 about the yaw axis, or any combination of these movements in the performance of clinical and medical functions. Changing the pitch, yaw, or grip of the instrument 4400 can be performed by manipulating the tension members.

The transmission 4700 produces movement of each of the first tension member 4420 and the second tension member 4430 to produce the desired movement (pitch, yaw, or grip) at the wrist assembly 4500. Specifically, the transmission 4700 includes components and controls to move some of the tension members in a proximal direction (i.e., to pull in certain tension members) while simultaneously allowing the distal movement (i.e., releasing or "paying out") of other of the tension members. In this manner, the transmission 4700 can maintain the desired tension within the tension members, and, in some embodiments, can ensure that the lengths of the tension members are conserved (i.e., moved in equal amounts) during the entire range of motion of the wrist assembly 4500.

Figure 8A:
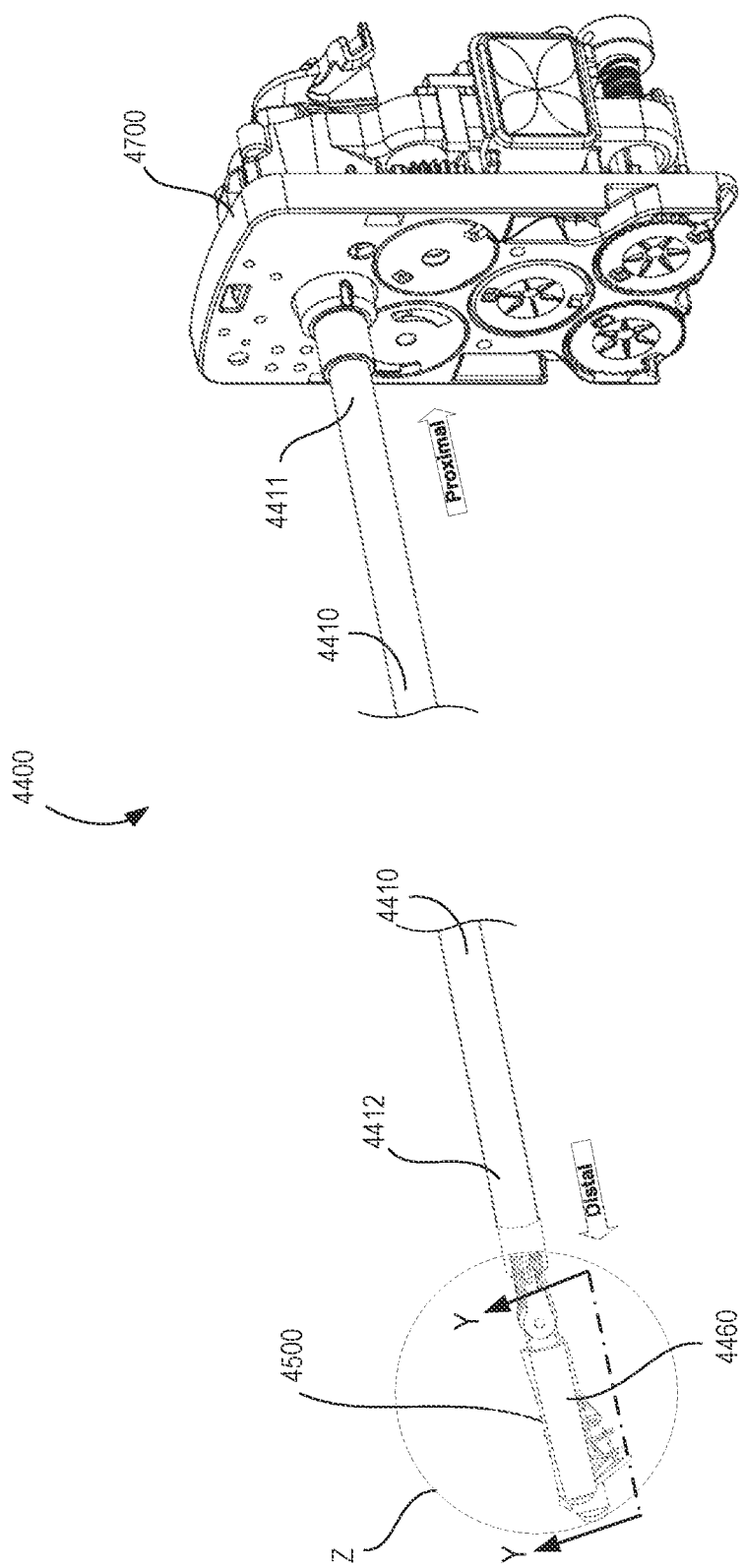
FIG. 8A is a perspective view of an instrument of a surgery system in a first orientation with a removable support apparatus attached, according to an embodiment.

The transmission 4700 includes a chassis 4760, a first capstan assembly 4710, a second capstan assembly 4720, a third capstan assembly 4730, a fourth capstan assembly 4740, a roll actuator 4750, and a tension member guide 4799. The chassis 4760 (which functions as a housing) provides the structural support for mounting and aligning the components of the transmission 4700. For example, as shown in FIG. 8A, the chassis 4760 defines a first opening within which the proximal end portion 4411 of the shaft 4410 is mounted, and multiple second openings within which the capstan assemblies are mounted. The chassis 4760 includes an upper housing 4765 that provides additional mounting surfaces and support (e.g., for the capstan assemblies).

The shaft 4410 can be any suitable elongated shaft that couples the wrist assembly 4500 and the end effector 4460 to the transmission 4700. Specifically, the shaft 4410 includes a proximal end portion 4411 that is coupled to the chassis 4760. The shaft 4410 defines at least one passageway through which the first tension member 4420, the second tension member 4430, and other components (e.g., energized electrical wires, ground wires, or the like, not shown) can be routed from the transmission 4700 towards the wrist assembly 4500. Moreover, although the chassis 4760 is shown as defining an opening within which the proximal end portion of an instrument shaft 4410 is mounted, in other embodiments, the shaft 4410 can be coupled to the chassis 4760 by any suitable mechanism (e.g., a flange connection). Although shown as being cylindrical, in other embodiments the shaft 4410 can have any suitable shape.

In addition to providing mounting support for the internal components of the transmission 4700, the chassis 4760 can also include external features (not shown, but which can be recesses, clips, etc.) that interface with a docking port of a drive device (not shown). The drive device can be, for example, a computer-assisted teleoperated surgical system that can receive the transmission 4700 and manipulate the transmission 4700 to perform various surgical operations. In other embodiments, the drive device can be an assembly system that can receive and manipulate the transmission 4700 to perform various assembly operations.

Figure 8B:
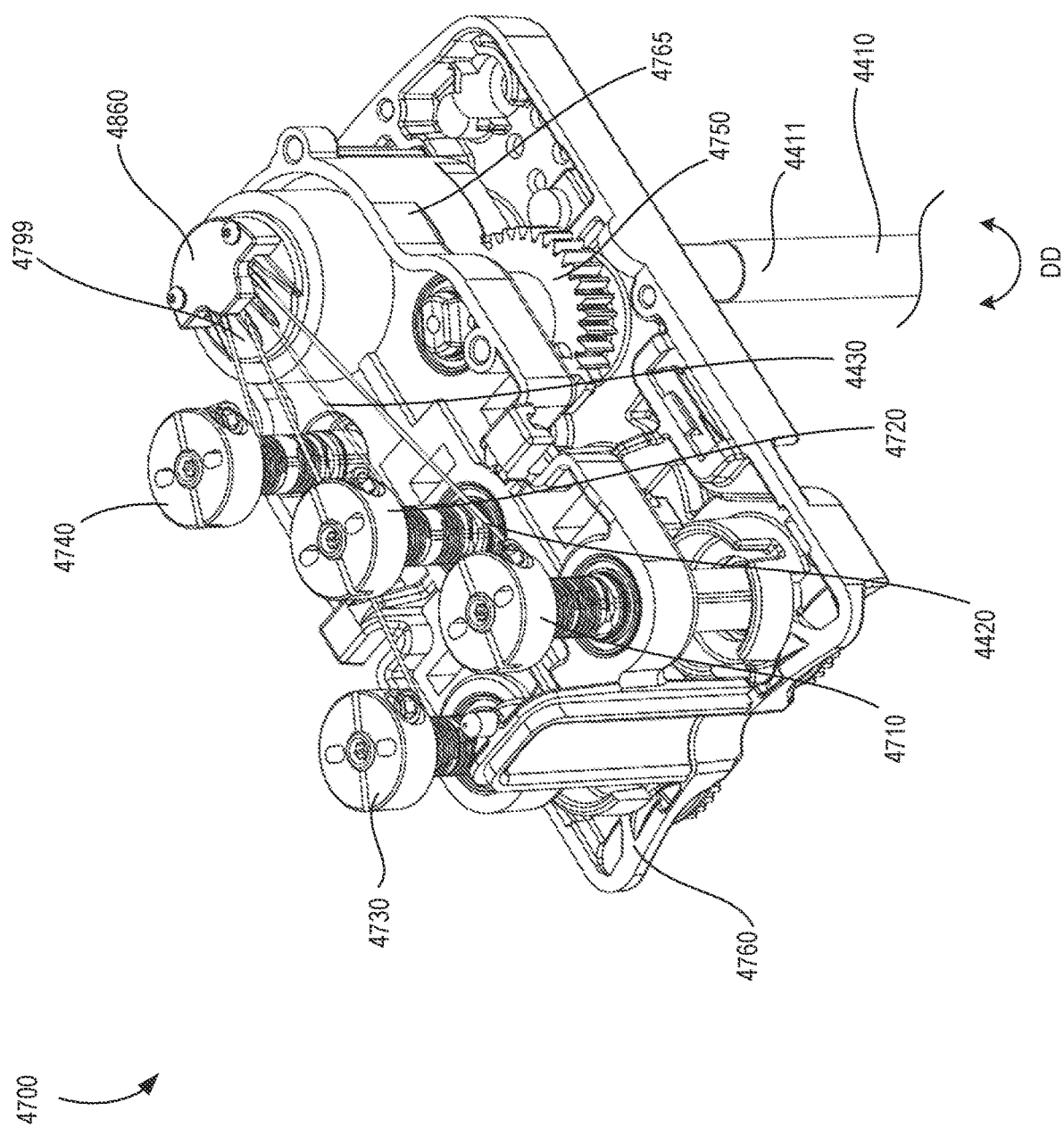
FIG. 8B is an enlarged perspective view of a transmission at the proximal end portion of the instrument shown in FIG. 8A.
Figure 9:
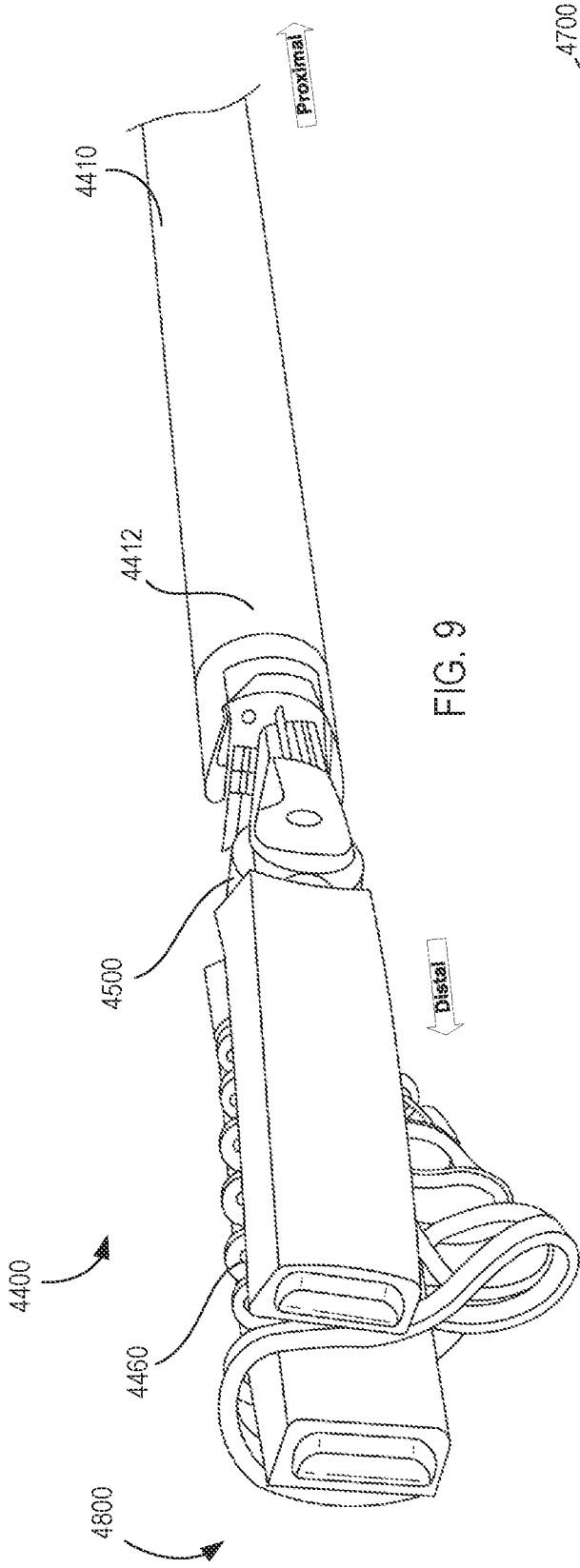
FIG. 9 is an enlarged perspective view of a distal end portion of the instrument assembly shown in FIG. 8A, according to an embodiment.

The first capstan assembly 4710 includes a shaft that can be motor-driven to rotate about a capstan axle. The rotating shaft includes a portion about which an end portion of the first tension member 4420 is wrapped. Thus, when the first capstan assembly 4710 rotates in a first direction, the first tension member 4420 can be moved proximally (i.e., can be pulled inward or wrapped about the rotating shaft), and when the first capstan assembly 4710 rotates in a second direction, the first tension member 4420 can be moved distally (i.e., can be payed-out or unwrapped from the rotating shaft). In a similar manner, the second capstan assembly 4720 includes a shaft about which an end portion of the second tension member 4430 is wrapped, and so on according to the number and arrangements of tension members appropriate for implementing desired medical and clinical functions. Referring to FIG. 8B, the arrangement of the capstan assemblies and the tension member guide 4799 defines a tension member path for each of the tension members. Through these tension member paths, the tension members are routed from their respective capstan assembly into the shaft 4410.

In some embodiments, the transmission mechanism 4700 includes components and controls to move some of the tension members in a proximal direction (i.e., to pull in certain tension members) while simultaneously allowing the distal movement (i.e., releasing or "paying out") of other of the tension members in equal lengths. In this manner, the transmission mechanism 4700 can maintain the desired tension within the tension members, and can ensure that the lengths of the tension members are conserved (i.e., moved in equal amounts) during the entire range of motion of the wrist assembly 4500. In some embodiments, for example, the transmission assembly 4700 can be any of the transmission assemblies shown and described in International Patent Application No. PCT/US2017/062258, (filed Nov. 14, 2017), entitled "Cable Length Conserving Medical Instrument," which is incorporated herein by reference in its entirety. In other embodiments however, conservation of the lengths of the tension members is not required.

Referring to FIGS. 9-13 and 15-18, the wrist assembly 4500 of the instrument 4400 includes the end effector 4460 and a distal clevis 4610. A proximal end 4611 of the distal clevis 4610 is articulably coupled to the instrument shaft, either directly or via a proximal clevis 4510 (that also functions as a link). A pin 4640 couples the proximal clevis 4610 to the proximal end 4611 of the distal clevis 4610. The distal clevis 4610 can rotate relative to the proximal clevis 4510 that is connected to the instrument shaft about pin 4640. In this manner, the distal clevis 4610 can be articulably coupled to the instrument shaft. A distal end 4612 of the distal clevis 4610 further includes a connector 4680 that is coupled to the end effector 4460. In this manner, the first tool member 4462 and the second tool member 4482 of the end effector 4460 can rotate relative to the clevis 4610 about a second axis of rotation, $A_2$. (also referred to as the yaw axis). The connector 4680 is a pin-type connector and includes a pin 4682 supported by (and placed within) the pin openings. In some embodiments, the connector 4680 can include any of the structure and features of the pinned joints shown and described in U.S. Pat. No. 9,204,923 B2 (filed Jul. 16, 2008), entitled "Medical Instrument Electronically Energized Using Drive Cables," which is incorporated herein by reference in its entirety. As shown in FIG. 8A, the second axis of rotation (also referred to as the yaw axis) is non-parallel to the pitch axis $A_1$. Thus, the instrument 4400 provides for up to three degrees of freedom (i.e., a pitch motion about the first axis of rotation $A_1$, a yaw rotation about a second axis of rotation, and a grip motion about the second axis of rotation).

As further shown in FIGS. 9-13 and 15-18, the end effector 4460 includes the first tool member 4462 (which functions as a first retractor blade 4462) and the second tool member 4482 (which functions as a second retractor blade 4482). The first retractor blade 4462 has a proximal end portion 4467 that is movably coupled to the distal clevis 4610 and an opposite distal end portion 4463. Similarly, the second retractor blade 4482 has a proximal end portion 4487 movably coupled to the distal clevis 4610 and an opposite distal end portion 4483. The first and second retractor blades 4462 and 4482 are each rotatably coupled to the distal clevis 4610 such that the second retractor blade 4482 can be moved relative to the first retractor blade 4462 between a closed orientation (FIGS. 11 and 12), and one or more second orientations (see e.g., FIGS. 15 and 16). The first retractor blade 4462 has a first tissue contact surface 4464 along a first side of the first retractor blade, and a third tissue contact surface 4465 along a second side of the first retractor blade. Similarly, the second retractor blade 4482 has a second tissue contact surface 4484 along a first side of the second retractor blade and a fourth tissue contact surface 4485 along a second side of the second retractor blade. (See FIGS. 13 & 15, which show the first and second tissue contact surfaces oriented away from the viewer). The first and second tissue contact surfaces 4464, 4484 on the first side of each of the first and second retractor blades 4462, 4482 are configured as the primary tissue contact surfaces for the retractor instrument 4400 for engaging tissue during clinical functions.

Figure 13:
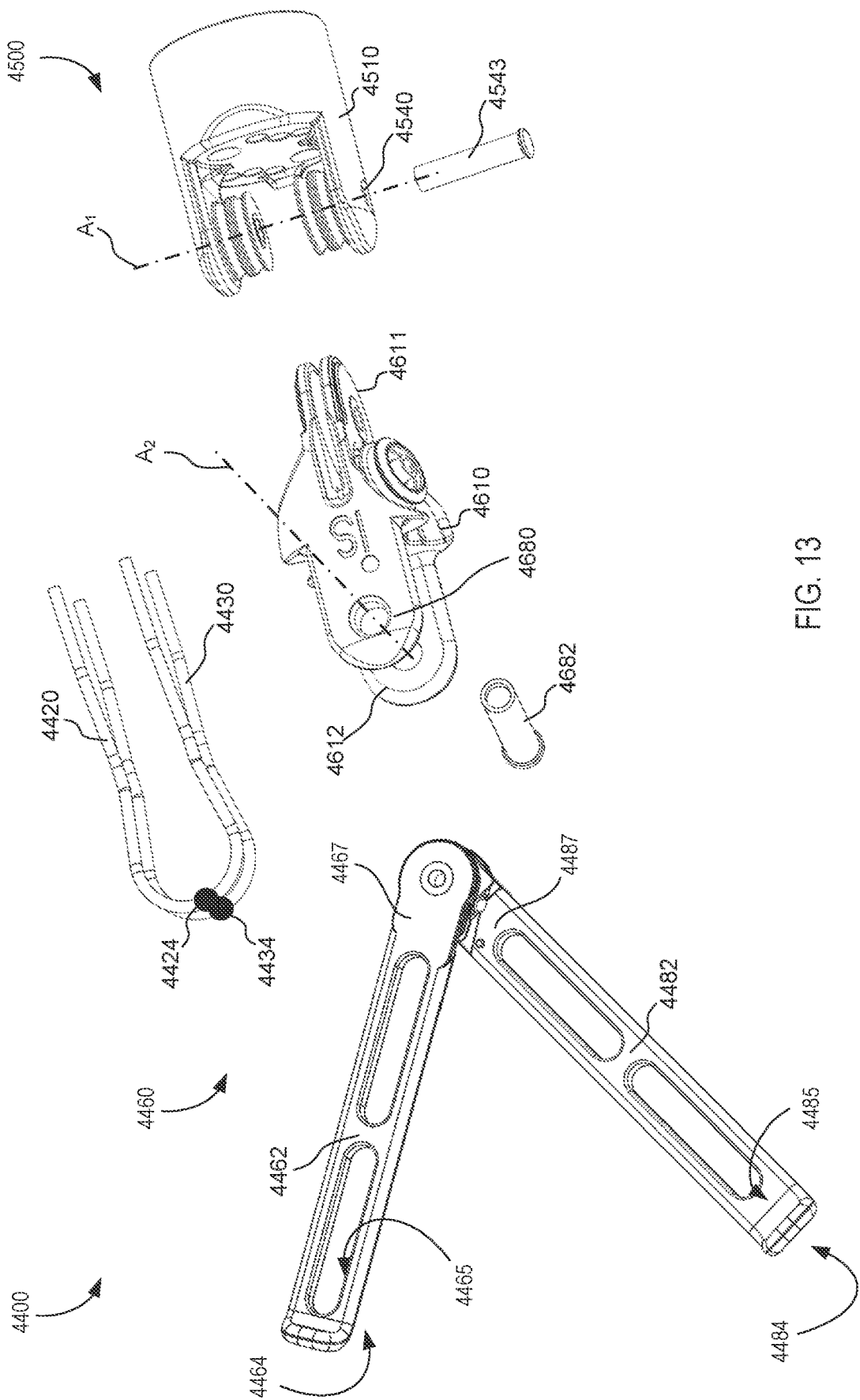
FIG. 13 is an enlarged perspective, exploded view of a distal end portion of the instrument indicated by the region Z shown in FIG. 8A, which is shown without the removable support apparatus.
Figure 15:
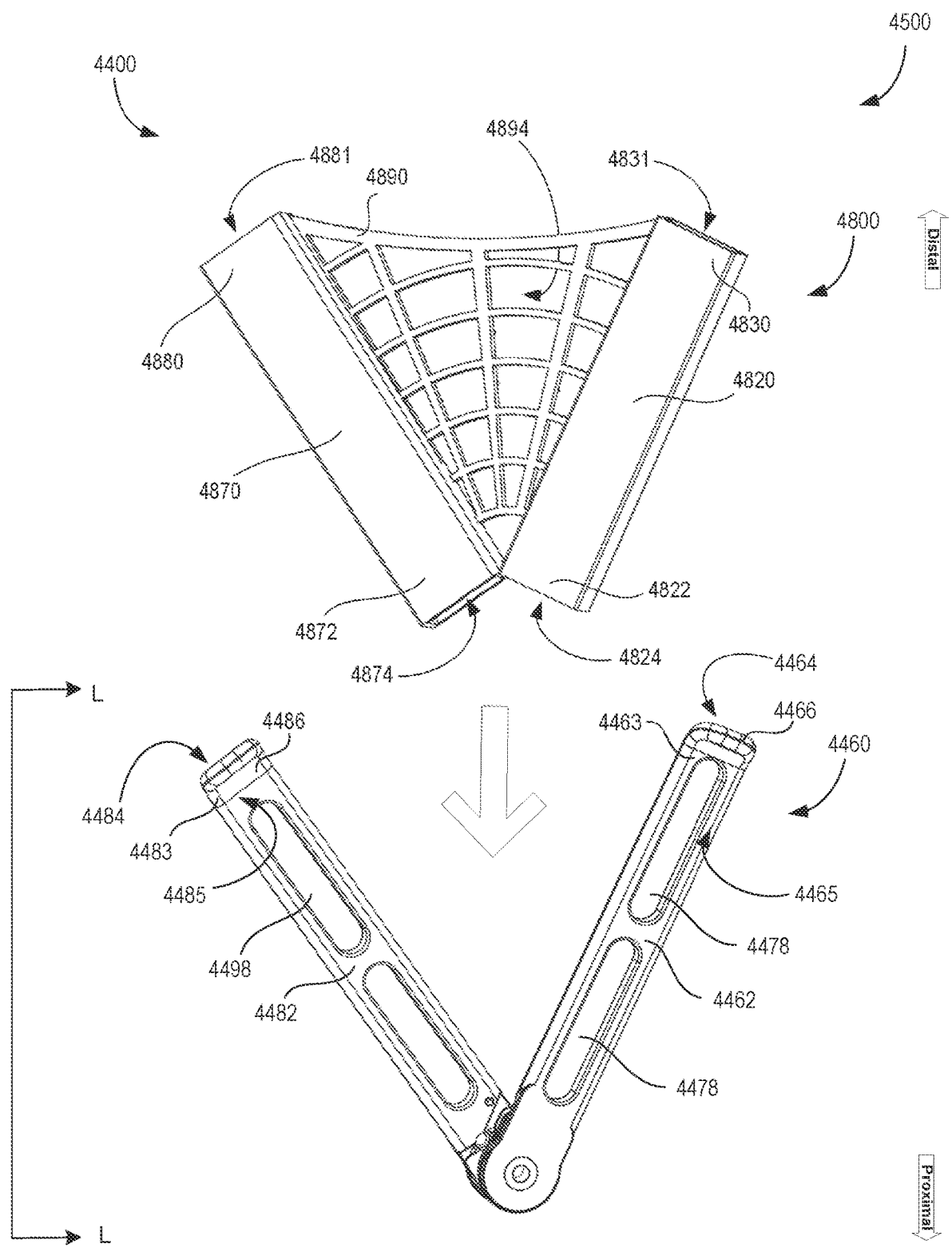
FIG. 15 is a front view of the removable support apparatus of FIG. 14A shown during attachment to a distal end portion of the instrument of a surgery system of FIG. 8A along with retractor blade portions of the instrument, according to an embodiment, which are shown in a second orientation.

As further shown in FIGS. 13 and 15, the first retractor blade 4462 includes a plurality of fenestrations 4478 formed therethrough along the length of the first retractor blade 4462. Similarly, the second retractor blade 4482 includes a plurality of fenestrations 4498 formed therethrough along the length of the second retractor blade 4482. The fenestrations 4478, 4498 are configured as large openings through the first retractor blade 4462 and the second retractor blade 4482. The fenestrations can be formed in the retractor instrument 4400 for various purposes including, for example, providing customized purchase for engaging a particular target tissue, such as for lifting or moving organs and large tissue masses for which it can be beneficial to concentrate forces along structural rib portions of the retractor blades that are formed by the large fenestrations for increase purchase with the tissue.

The fenestrations 4478 are shown as examples for options pertaining to the retractor tool configuration and its engagement with target tissue that can be modified by coupling support apparatus 4800 with the retractor instrument 4400. It is understood that fenestrations can be formed through one or more retractor blades and can include openings through the blades having a wide variety of shapes, patterns, numbers, spacings and arrangements formed through the blades, as well as retractor blades that lack any fenestrations and otherwise have various configurations that affect tissue interactions. The fenestrations can be formed in the retractor blades to modify the blade's purchase with target tissue during clinical functions, apply suitable force concentrations, retain particular types of tissues (e.g., larger tissues) while allowing other tissues (e.g., smaller tissues and fluids) to pass through the fenestrations, and for other reasons pertaining to the design and functions of the retractor tool 4400 and engagement with target tissue. Further, as discussed above along with support apparatus 3800, retention features of the support apparatus 4800 can take advantage of retractor blade fenestrations for enhanced coupling and retention of the support apparatus with the blade. As an example, the first and second sleeves 4820, 4870 can include internal projections, interference features, or other retention enhancement features (not shown) that are configured to engage the fenestrations or other features of the retractor blades in an advantageous manner. In other embodiments, the first retractor blade 4462 and the second retractor blade 4482 need not include fenestrations.

Figure 16:
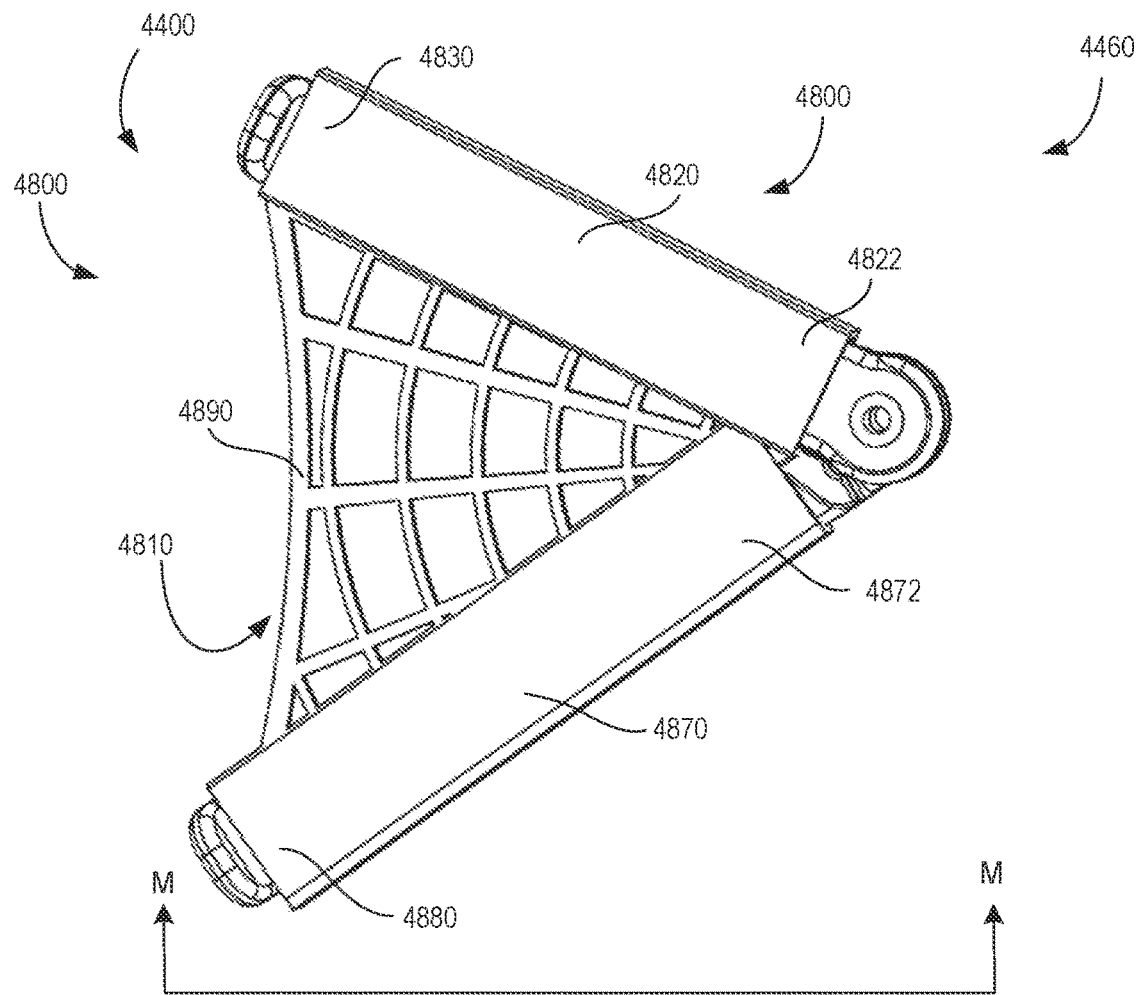
FIG. 16 is a front view of the removable support apparatus of FIG. 14A shown attached to the retractor blade portions of the instrument assembly of FIG. 8A, according to an embodiment, which are shown in the second orientation.

The tissue manipulation accessory 4800 (also known as the support apparatus) is configured to be selectively coupled with the retractor instrument 4400 and to be retained in the coupled state with the instrument as it performs clinical functions, such as retractor functions. Referring now to FIGS. 14A-18, the support apparatus 4800 includes a first sleeve 4820, a second sleeve 4870, and a flexible contact member 4890 extending between the first and second sleeve. The flexible contact member is coupled to each of the first sleeve and the second sleeve, and is configured to be moved between a collapsed configuration and an expanded configuration when coupled to the instrument based on the movements and orientations of the retractor instrument 4400. For example, FIGS. 9-12 show the support apparatus 4800 coupled to the retractor instrument 4400 and oriented with the instrument in a collapsed, closed orientation when the retractor blades 4462, 4482 of the instrument 4400 are likewise in a closed orientation. In addition, FIG. 16 shows the support apparatus 4800 coupled to the instrument 4400 and similarly oriented with the instrument in an open orientation. The open orientation can be the same orientation for the instrument 4400 and support apparatus 4800 shown in FIG. 15, in which the support apparatus and instrument are at least in a partially open orientation to facilitate coupling the support apparatus with the instrument, or a fully extended open orientation (not shown) with the retractor blades at their greatest angular rotation from each other, or another open orientation, such as can be suitable for various retractor functions.

Referring to FIG. 15, the first sleeve 4820 is configured to be coupled to the first retractor blade 4462, and the second sleeve 4870 is configured to be coupled to the second retractor blade 4482 via an overlap or overlay arrangement with the retractor blades. In particular, the first sleeve 4820 is configured to be placed about a portion of the first retractor blade 4462 including about a portion of the first tissue contact surface 4464 of the blade. Likewise, the second sleeve 4870 is configured to be placed about a portion of the second retractor blade 4482 including about a portion of the second tissue contact surface 4484. In order to facilitate placing each of the first and second sleeve 4820, 4870 in a position to receive the corresponding retractor blade 4462, 4482 and to slide over the length of each blade to surround portions of the blade along its length as described in greater detail below, the retractor instrument 4400 can be oriented in an open orientation such that the second retractor blade 4482 is angularly rotated apart from the first retractor blade 4462.

Figure 14A:
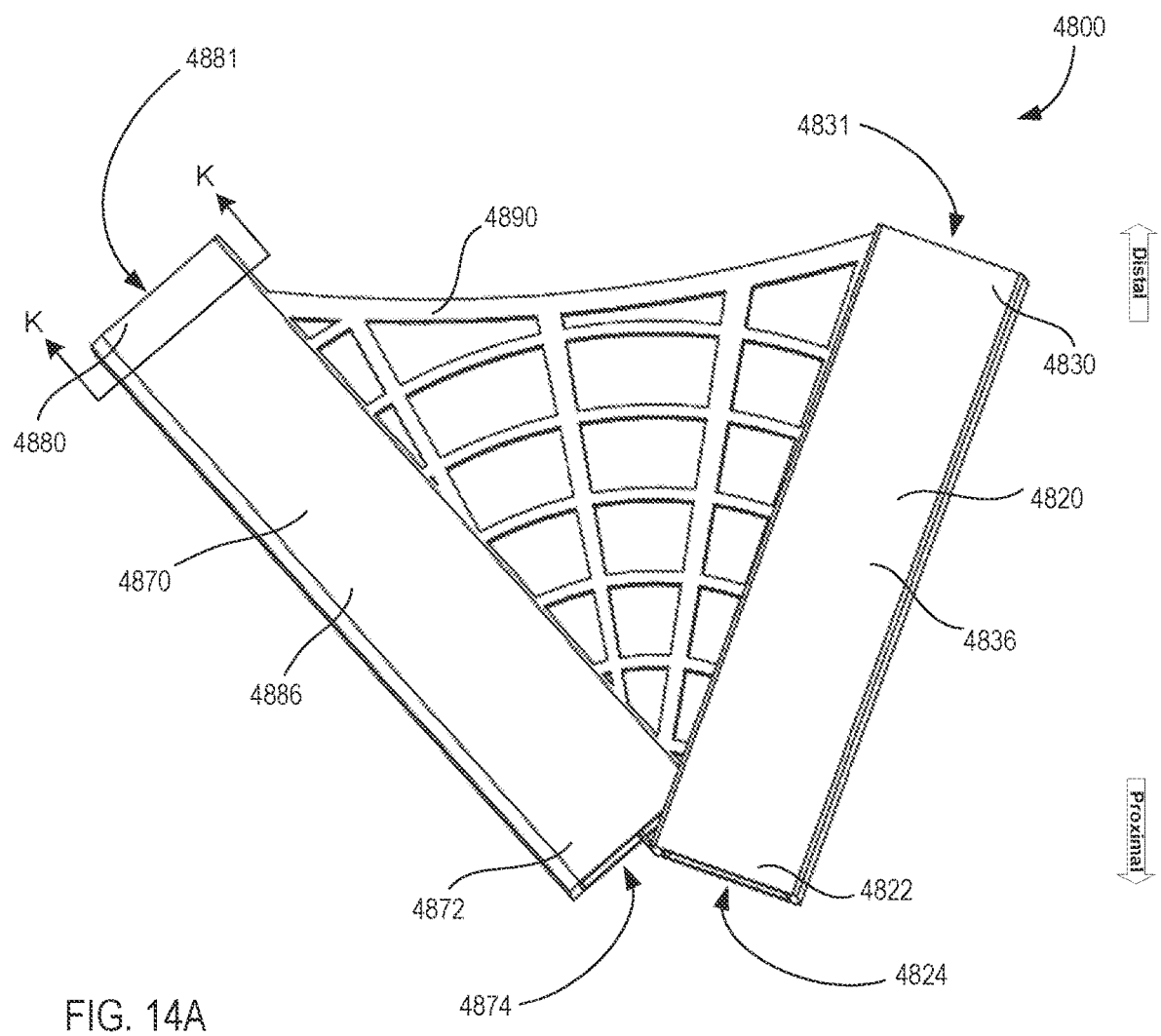
FIG. 14A is a front view of the removable support apparatus attached to the instrument of FIG. 8A, according to an embodiment.
Figure 14B:
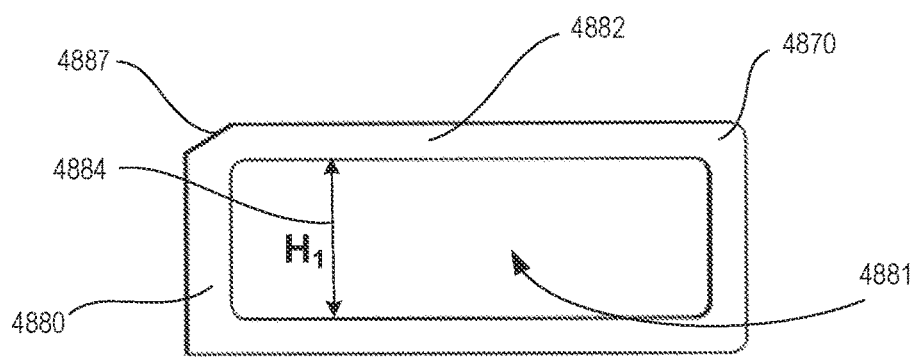
FIG. 14B is a cross-sectional view of a portion of the removable support apparatus of FIG. 14A, as viewed from line K-K shown in FIG. 14A.

Referring to FIGS. 14A and 14B, the first sleeve 4820 and the second sleeve 4870 are each configured as elongate members. As shown in FIG. 14A, the first sleeve 4820 extends in the elongate direction of the sleeve from a proximal portion 4822 at one end to a portion 4830 at the opposite end, with an intermediate portion 4836 disposed therebetween. The first sleeve defines a pocket 4831 that is configured to receive the first retractor blade 4462 and to surround the portion of the first tissue contact surface 4464 about which the first sleeve is placed. The proximal end portion 4822 of the first sleeve 4820 also defines an opening 4824 into the pocket 4831 and as an entry through which the pocket 4831 can be accessed. The second sleeve 4870 extends in the elongate direction of the sleeve from a proximal portion 4872 at one end to a distal portion 4880 at the opposite end, with an intermediate portion 4886 disposed therebetween. The second sleeve defines a pocket 4881 that is configured to receive the second retractor blade 4482 and to surround the portion of the second tissue contact surface 4484 about which the second sleeve is placed. The second sleeve 4870 also defines an opening 4874 into the pocket 4881 and as an entry through which the pocket 4881 can be accessed. In some embodiments, each of the first and second sleeves 4820, 4870 can surround a portion of the corresponding retractor blade along with the first and second tissue contact surfaces. This arrangement can provide benefits including greater attachment with and retention to the corresponding retractor blade that the sleeve surrounds. Such an arrangement can also provide enhanced tissue interface characteristics based on the enhanced attachment, as well as from optional tissue engagement features of the sleeves, such as surface texture, grip patterns, and related features that can affect tissue purchase.

Figure 12:
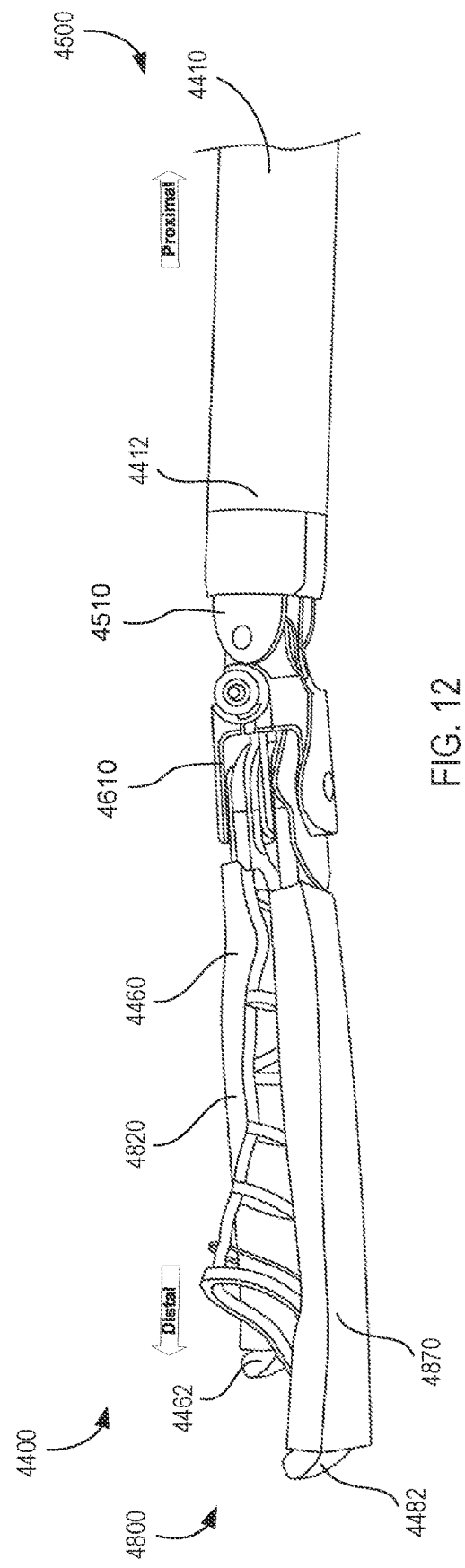

FIG. 14B shows a cross-sectional view of the second sleeve 4870 taken at its distal portion 4880, as indicated by line K-K shown in FIG. 14A. Although only the second sleeve is shown in FIG. 14B, it is understood that the first sleeve is configured in a similar manner and generally includes similar aspects and features as the second sleeve, except as discussed herein. Further, the first sleeve 4820 can optionally be configured to have a mirror image with respect to the second sleeve cross-section configuration described herein. It is further understood that different variations (not shown) can optionally exist between the first and second sleeves 4870, 4820, such as differences to accommodate variations between each of the retractor blades 4462, 4482 including differences in their lengths or other dimensions. Although shown in FIG. 14B as a generally rectangular cross-sectional shape, each of the sleeves 4862, 4882 can define any suitable pocket shape or other arrangement of features for removably coupling each sleeve with the corresponding retractor blade. As shown in FIG. 12, in some embodiments each of the first and second sleeves 4820, 4870 can be formed from a plurality of flexible, resilient walls that are configured to form a tight, conforming fit about the corresponding retractor blade 4462, 4482, such that the contours of each sleeve along its length adapts to follow the lengthwise contour of the corresponding retractor blade when coupled to the retractor tool 4400.

Moreover, as shown, each of the first sleeve 4820 and the second sleeve 4870 have a length in the elongate direction that is equal to or less than a length of the corresponding retractor blade to which it is coupled. In some embodiments, the length of each of the first and second sleeve 4820, 4870 is at least one-half the length of the corresponding retractor blade, which can securely retain the support apparatus in the coupled attachment position with the instrument 4400 during use. In some embodiments, the length of each of the first and second sleeve 4820, 4870 is at least three-fourths the length of the corresponding retractor blade, which can even more securely retain the support apparatus with the instrument, as well as provide enhanced tissue interface benefits as described below along with the flexible support member 4890. Although the first sleeve 4820 and the second sleeve 4870 are each shown as defining a pocket, in other embodiments, each of the sleeves can be configured to include other attachment configurations that do not fully enclosed the retractor blades (see FIGS. 7A and 7B).

Figure 17:
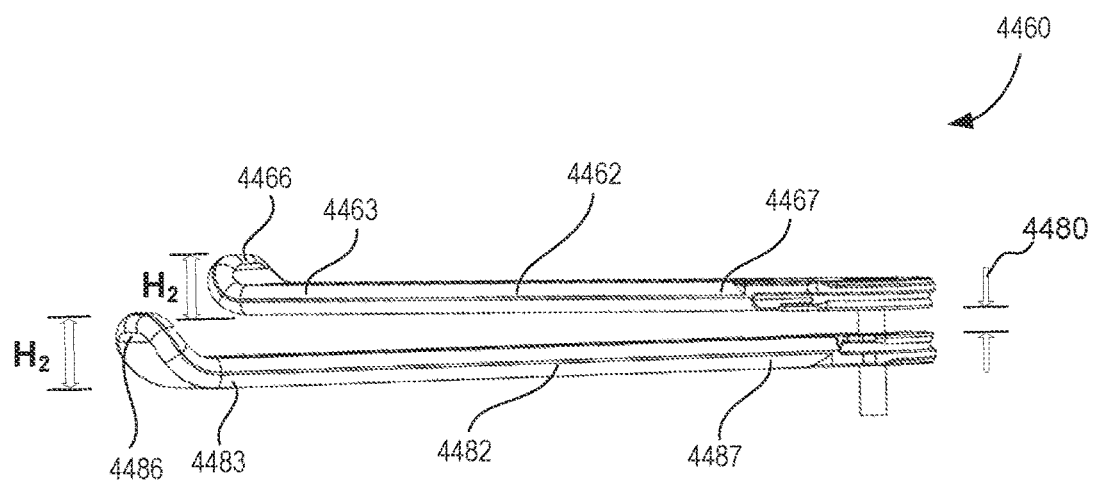
FIG. 17 is a side view of the retractor blade portions of the instrument of FIG. 8A as viewed from line L-L in FIG. 15.
Figure 18:
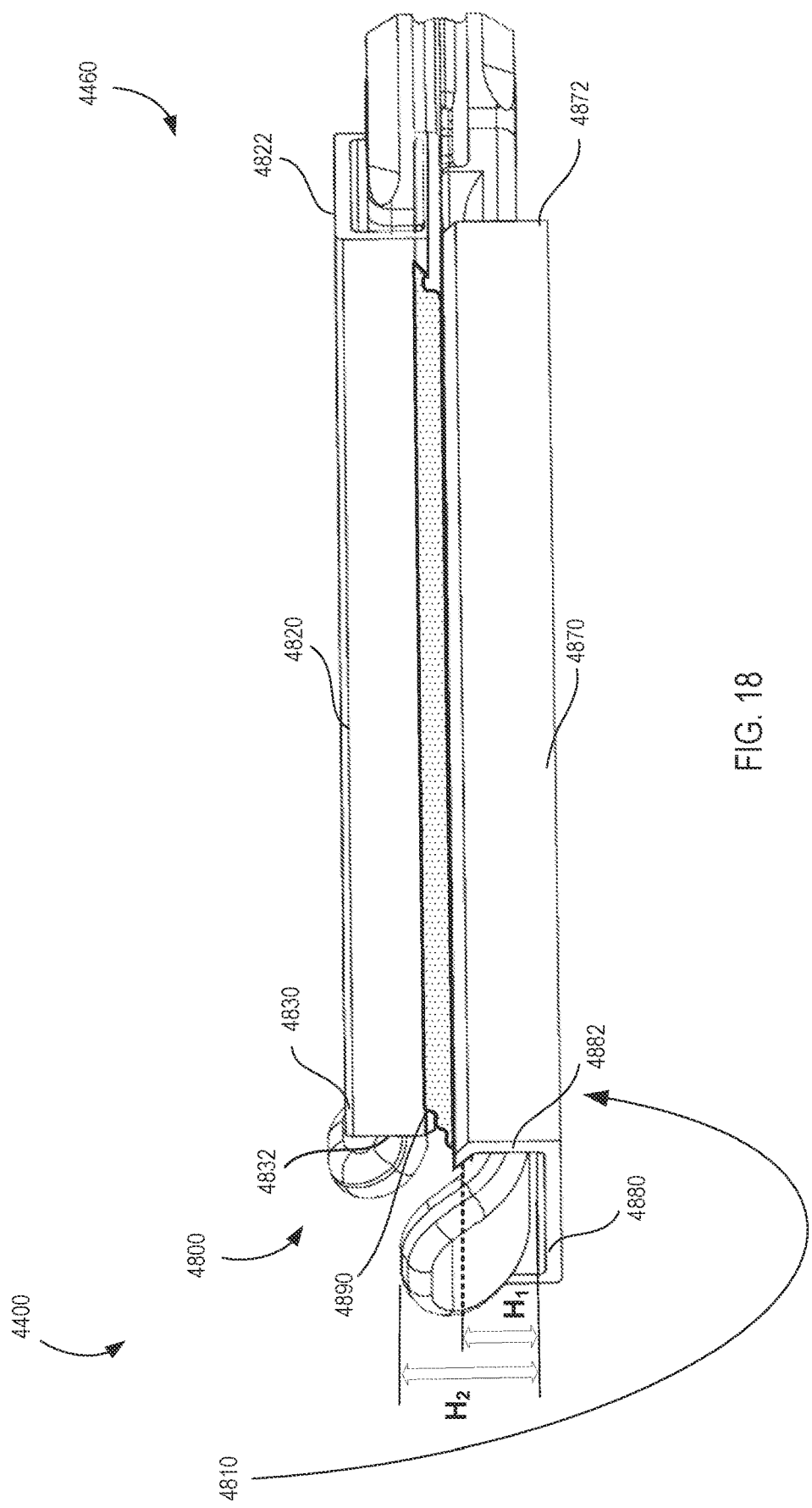
FIG. 18 is a side view of the removable support apparatus assembly of FIG. 16 as viewed from line M-M in FIG. 16.

Referring to FIGS. 15-18 along with FIG. 6, the support apparatus 4800 can be coupled to the retractor instrument 4400 in a manner similar to the method 100 described above along with FIG. 6 and as described above along with FIG. 15 in accordance with configurations and features of the support apparatus 4800 and the surgical instrument 4400. As such, each of the first and second sleeves 4820, 4870 receive the corresponding retractor blade 4462, 4482 into the corresponding pocket 4831, 4881 via openings 4824, 4874 at the corresponding distal portion 482, 4872, such that each sleeve extends about the corresponding retractor blade to surround a portion of the blade along its length. Stated differently, each of the first and second sleeves 4820, 4870 are coupled to the corresponding retractor blade 4462, 4482 in a linear, coaxial orientation such that each sleeve surrounds a portion of the corresponding elongate blade along its blade length including extending about the first tissue contact surface 4464 of the first retractor blade and about the second tissue contact surface 4484 of the second retractor blade.

It is understood that the first and second sleeves 4820, 4870 can include a wide variety of additional configuration options in accordance with, for example, features of the surgical instrument to which the support apparatus is configured to couple, tissue interface characteristics of the instrument, and the type of clinical functions to be performed. For example, the cross-sectional shape shown in FIG. 14B is a generally rectangular shape that is configured to couple with the corresponding retractor blades 4462, 4482 of the retractor instrument 4400 that also have a generally rectangular cross-section. As another example shown in FIG. 14B, an optional orientation feature 4887 can be formed on one or both sleeves 4820, 4870, which can guide the clinician with respect to proper orientation of the support apparatus 4800 relative to the instrument 4400 when coupling the support apparatus to the retractor tool. In a further example shown in FIG. 12, the interior dimensions of each sleeve 4820, 4870 can be configured to tightly conform to dimensions of the corresponding retractor blade such that the contour of each sleeve closely follows the blade contour along its length, which can enhance coupling and retention of each sleeve to the corresponding blade. In addition, various sleeve dimensions can be configured to provide an interference fit with features of the corresponding retractor blade that can enhance attachment of the sleeve to the corresponding blade, as well as form one or more retention members enhancing retention of the sleeve on the blade.

Referring to FIG. 14B along with FIG. 17, as another example the distal portions 4830, 4880 of each sleeve 4820, 4870 are configured to have height, $H_1$, in a relaxed state and/or when coupled with the corresponding retractor blade 4462, 4482, which is less than a tip height, $H_2$, of the curved tip 4466, 4486 at the distal portion of the corresponding retractor blade 4462, 4482. Further, each of the sleeves 4820, 4870 is configured to have sufficient flexibility and resiliency along its walls 4838, 4888 such that each of the sleeves is able to stretch and flex as needed during installation around the corresponding retractor blade 4462, 4482. Thus, as shown in FIG. 18 when each of the sleeves 4820, 4870 are coupled to the corresponding retractor blade 4462, 4482, the inner height, Hi, of each sleeve at its distal portion forms a retention member 4432, 4482, which retains the sleeve in its coupled attachment position with the corresponding retractor blade. In the event translation forces are applied to one of the sleeves 4820, 4870 to move the sleeve in a distal direction along the length of its corresponding blade, the retention member 4432, 4482 is configured to interfere with the tip portion of the corresponding retractor blade. As such, each retention member 4432, 4482 forms a stop to prevent inadvertent removal of the sleeve 4820, 4870 during use, such as when performing retractor functions and during insertion and withdrawal of the coupled support apparatus 4800/retractor tool 4400 through a cannula 4314 (FIG. 10) providing access to the surgical environment.

As such, the first and second removable connectors 4420, 4470 can be securely attached and retained to the first and second retractor blades 4462, 4482 during use of the support apparatus 4800 when in a coupled assembly condition with the retractor instrument 4400, as well as be easily attached and removed as desired. Thus, the flexible contact member 4890 can be attached to the first sleeve 4820 at a region that covers a portion of the first tissue contact surface 4464 of the first retractor blade 4462, and to the second sleeve 4870 at a region that covers the second tissue contact surface 4484, such that a first contact surface 4494 of the flexible contact member 4490 cooperates with the first and second removable connectors along a first outer side 4810 of the support apparatus to modify engagement of the retractor tool 4400 with target tissue.

Figure 10:
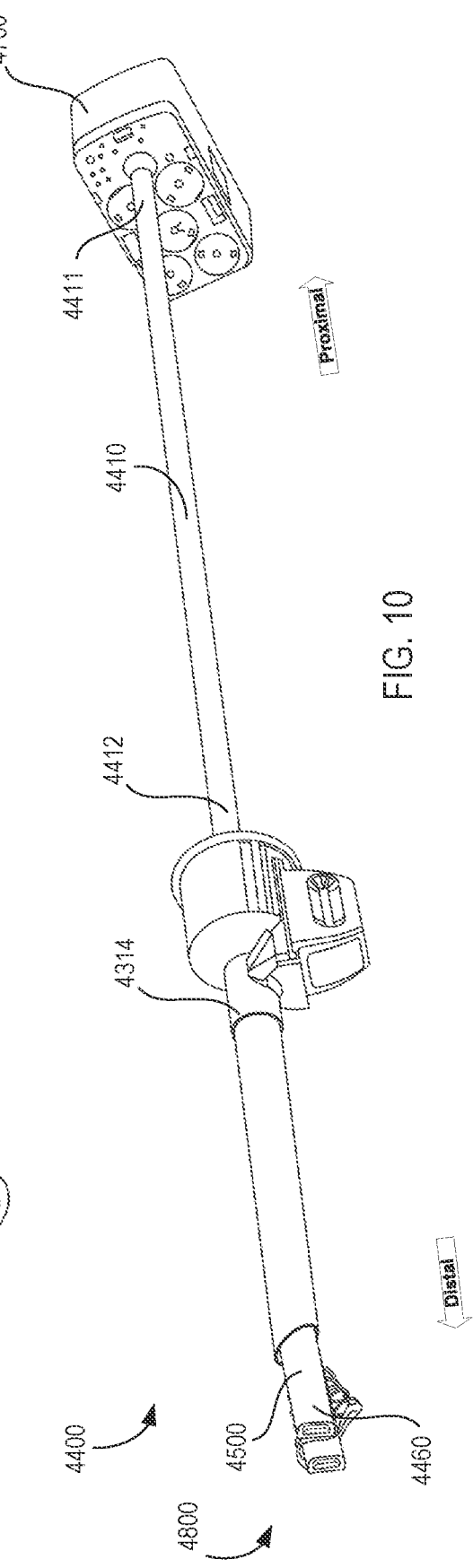
FIG. 10 is a perspective view of the instrument assembly of FIG. 8A shown in the first orientation during installation of the assembly through a cannula for entry into a surgical environment, according to an embodiment.
Figure 11:
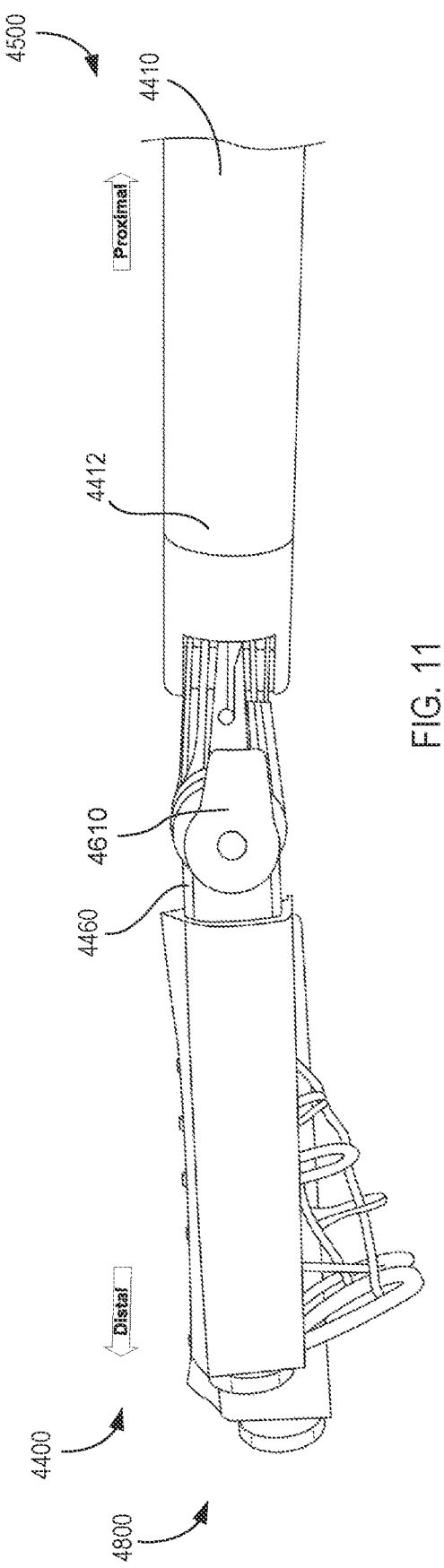
FIGS. 11 and 12 are front and side views respectively of the distal end of the instrument assembly of FIG. 8A indicated by region Z in FIG. 8A shown in the first orientation.

Stated differently, as shown in FIGS. 16-18, a first outer side 4810 of the support apparatus 4800 is configured to be disposed between the first and second tissue contact surfaces 4464, 4484 of the retractor tool 4400 and a target tissue during usage, which modifies the engagement of the retractor tool 4400 with the tissue. The first outer side 4810 includes a first contact surface 4494 of the flexible contact member and outer surfaces of the first and second sleeves 4820, 4870 that cover the first and second tissue contact surfaces 4464, 4484. The flexible member 4890 is configured to move to a collapsed configuration when the tissue manipulation accessory 4800 is coupled to the instrument and the instrument is in the closed orientation. As such, similar to flexible member 2890, the flexible member 4890 is configured to have sufficient flexibility so that it can bend, fold, roll and otherwise collapse into a compact collapsed configuration that can fit within spaces 4480 between the first and second sleeves 4820, 4870 and retractor blades 4462, 4482 and/or roll, fold or otherwise move close to the sleeves to which the flexible member is coupled. Further, as shown in FIG. 10 and as discussed above along with FIG. 6, the flexible member 4890 is configured to have sufficient flexibility to collapse, fold or flex as needed when being advanced or withdrawn through a cannula 4314 to access the surgical environment.

As described along with other embodiments herein, the flexible member 4890 can be configured and formed from various materials and arrangements, which can provide various characteristics for the tissue manipulation accessory as appropriate for the surgical environment and clinical functions. As shown in FIGS. 14A, 15 and 16, similar to support apparatus 3800, the flexible member 4890 is configured to have a spider-web type pattern extending radially outward in the region between the first retractor blade 4462 and the second retractor blade 4482. As such, the flexible contact member 4890 includes a series of elongate lateral rings extending from the first retractor blade 4462 to the second retractor blade 4482, as well as a series of elongate radial supports extending distally outward from a central portion near the clevis 4610 and connecting the lateral rings. Thus, the flexible contact member 4890 forms an interconnected support web between the first and second retractor blades 4462, 4482, which can effectively interface with tissue and organs when performing retractor functions, such that the support apparatus 4800 including the flexible member 4890 modify interfacing contact of the surgical retractor 4400 with tissue during use. For instance, flexible contact member 4890 can increase the area of retractor contact with the tissue during use of the support apparatus 4800 when coupled to the instrument 4400, by extending between the retractor blades 4462, 4482 and interfacing with tissue between the blades during retractor functions. Further, the flexible contact member 4890 can enhance the retractor contact during clinical functions versus the contact provided by the instrument 4400 alone, such as by spreading contact forces along the increased contact area, which can avoid tissue damage from applying concentrated forces with the first and second retractor blades alone. In addition, surface features of the flexible contact member 4890, including texture and grip features along its first contact surface 4894 and its structural, web-like arrangement, can modify purchase of the surgical retractor 4400 coupled with the support apparatus 4800 when engaging tissue.

Thus, a beneficial tissue manipulation accessory is provided via the support apparatus 4800 that can easily and removable be selectively coupled with the surgical retractor 4400 as appropriate for the surgical environment. The support apparatus 4800 can be securely retained with the surgical instrument during use including during installation and withdrawal via a cannula to the surgical environment. The support apparatus 4800 can modify tissue interface features of the surgical retractor as appropriate to enhance its performance of clinical functions. As noted above, it is understood that the support apparatus 4800 can be configured to be attached to multiple variations and types of surgical tools, such as to be coupled with multiple arrangements of surgical retractors. As an example, FIG. 19 shows a support apparatus 5800 that is generally the same as support apparatus 4800, but which is shown being coupled with a different configuration of a retractor tool 5400.

Figure 19:
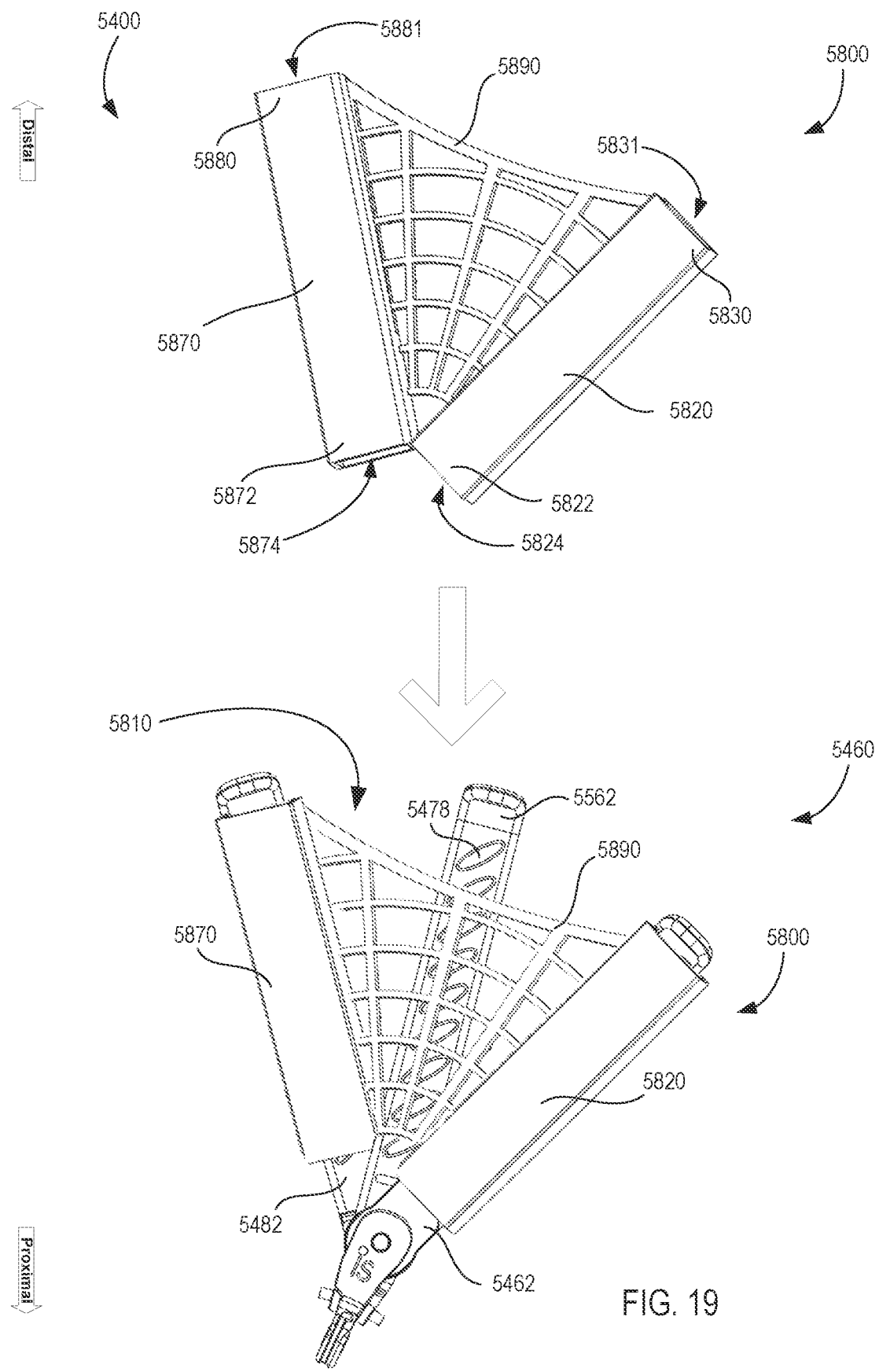
FIG. 19 is a front view of the removable support apparatus of FIG. 14A attached to a distal end portion of an instrument of a surgery system having three retractor blades, according to an embodiment.
Figure 21:
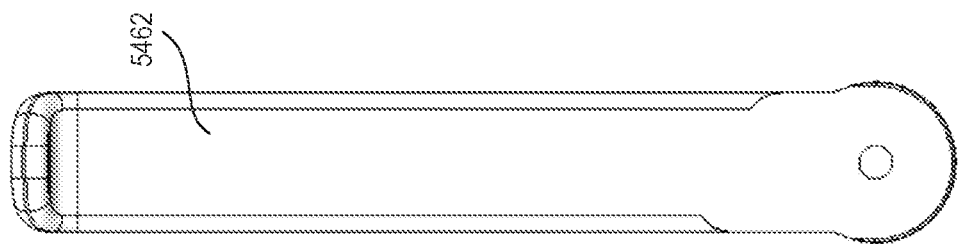
FIGS. 20 and 21 are front views of optional arrangements of surgical retractor blades for use with the removable support apparatus assembly of FIG. 8A, according to embodiments.

Referring to FIG. 19, support apparatus 5800 is shown being coupled with a surgical retractor 5400, according to an embodiment. Each of support apparatus 5800 and retractor tool 5400 include the same aspects, features and characteristics as support apparatus 5800 and retractor tool 5400, except as described herein. As such, like numbers refer to like features. As shown in FIG. 19, the retractor tool 5400 includes an additional third retractor blade 5562 at an intermediate position between the first retractor blade 5462 and the second retractor blazed 5482. In other embodiments for the surgical retractor (not shown), the surgical retractor can include multiple intermediate retractor blades between the first and second retractor blades. Embodiments pertaining to surgical retractor tools having three or more expandable retractor blades are described in greater detail in copending U.S. Provisional Application No. 62/767,661, entitled "Medical Devices Having Multiple Blades and Methods of Use," filed Nov. 15, 2018, which is incorporated herein by reference in its entirety.

As shown in FIG. 19, support apparatus 5800 can be configured to be coupled with retractor tool 5800 in a similar manner as described above for retractor tool 4800. As illustrated, the support apparatus can include a first sleeve 5820 configured to be coupled with the first retractor blade 5462, a second sleeve 5870 configured to be coupled with the second retractor blade 5482, and a flexible contact member 5890 extending between the first and second sleeve. When coupled with surgical retractor 5400, the flexible contact member 5890 can be configured to extend across either side of the third retractor blade 5562 as desired by the clinician in accordance with the surgical environment. For instance, in some instances it can be beneficial for the third retractor blade 5562 to directly engage a particular portion of tissue, such as a particular organ, while the first tissue contact surface 5810 of the flexible contact member engages other surrounding tissue on each side of the third retractor blade 5562. In other instances, it can be more beneficial for the flexible contact member 5890 to extend around the same side of all three retractor blades to modify overall tissue engagement of the surgical retractor 5400 with the target tissue. As such, the support apparatus 5800 is configured to be coupled with the surgical instrument 5400 via attachment of its first and second sleeve with the outer first and second retractor blades without rigid attachment to the third retractor blade 5562. In other words, the flexible contact member 5890 is configured without having a firm connection to the third retractor blade 5562. Thus, the clinician is free to place the flexible contact member 5890 on either side of the third retractor blade 5562 when coupling the support apparatus to the surgical retractor 5400.

Figure 20:
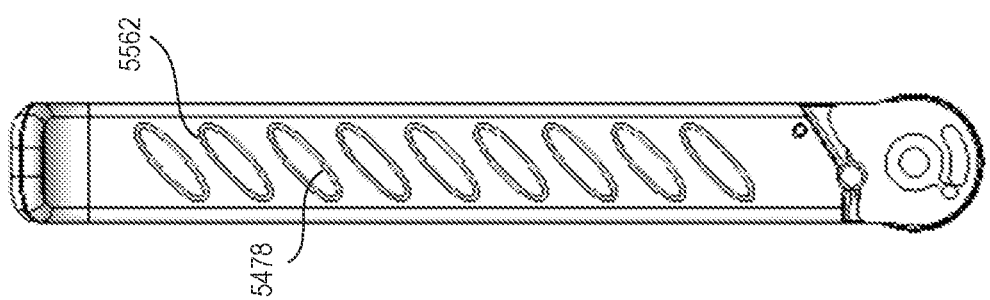

Optionally, the support apparatus 5800 could include features for securely attaching to the third retractor blade 5562. For example, as shown in FIGS. 19 and 20, the third retractor blade 5562 can include a plurality of angled, fenestration slots 5478 similar to those described above along with support apparatus 3800, which can optionally be formed through the through retractor blade to provide different tissue purchase and fluid flow with respect to the central, third blade vs. the first and second retractor blades. In a similar manner as described above for support apparatus 3800, the support apparatus could include features configured to engage the fenestrations 5478 for enhanced attachment and retention of the support apparatus when coupled with the retractor tool 5400. It is further understood that multiple other optional attachment, retention, and coupling features can be included with the support apparatus as appropriate in accordance with, for example, the surgical tool, intended usage, and surgical environment.

In addition, it is understood that various other options, variations, arrangements and configurations can included with embodiments of the support apparatus described herein without departing from the scope of those embodiments. As discussed above along with support apparatus 5800, many such options can be included in accordance with particular features and configurations of the surgical instrument with which the support apparatus is configured to be coupled. For instance, as discussed above along with support apparatus 5800, the support apparatus is configured to be coupled with various configurations of extendable retractor tools, such as with configurations having a central, third retractor blade and configurations having multiple central retractor blades.

It is further understood that aspects and features of the support apparatus embodiments described herein also include many different and varied options, features, materials, textures, structural arrangements for the support apparatus overall and, in particular, for the flexible support member, that can modify engagement of the surgical tool with target tissue when the support apparatus is coupled to the tool. As examples, FIGS. 22-24 each show a different embodiment of a support apparatus 6800, 7800, 8800, and 9800, which are each similar to support apparatus 4800 described above, as well as being similar to each other and to support apparatus 5800. Thus, each of these embodiments generally include the aspects, features and other characteristics described above along with embodiments 4800 and 5800 except as described herein. As such, like numbers refer to like features.

Figure 22:
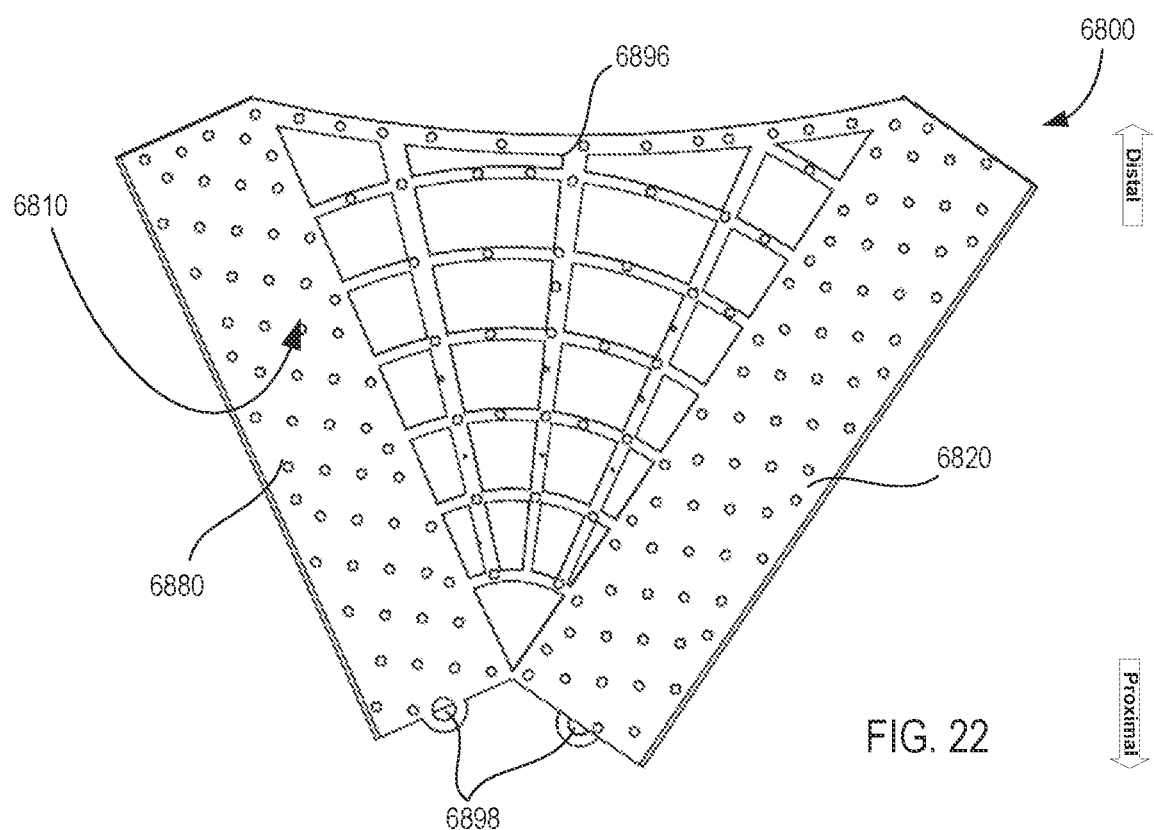
FIGS. 22-25 are front views of optional configurations of a removable support apparatus configured to be attached to an instrument of a surgery system, according to embodiments.
Figure 23:
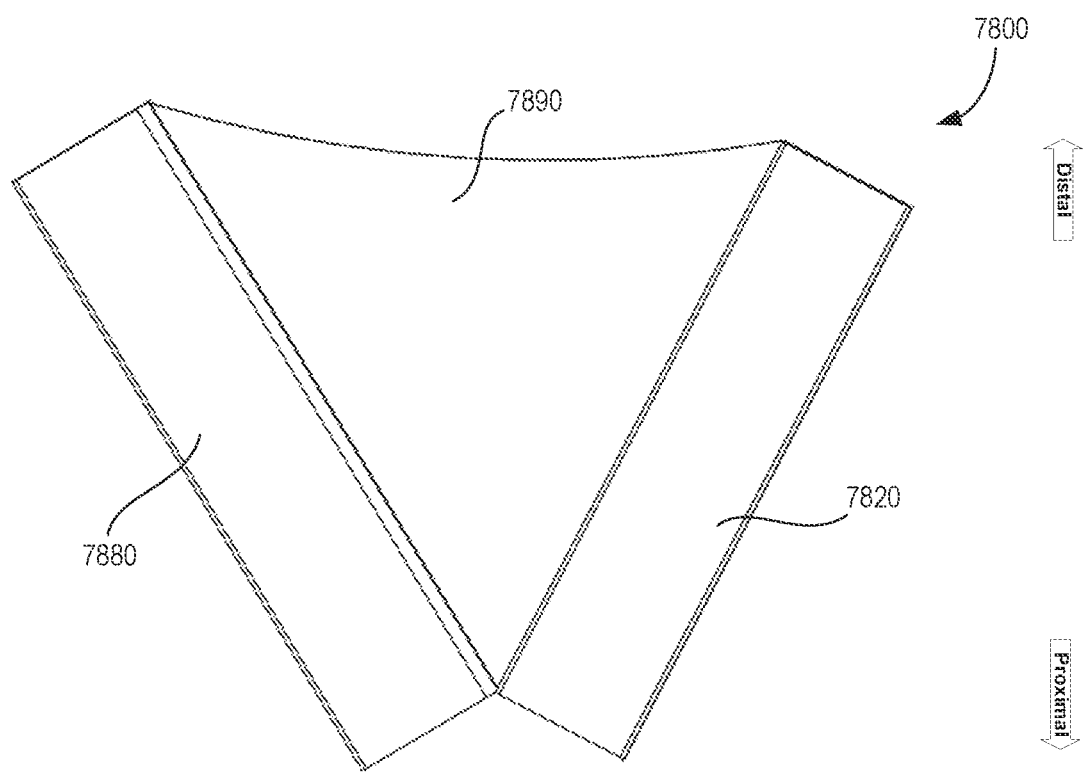

Referring to FIG. 22, an embodiment of a support apparatus 6800 is shown in an orientation such that the first tissue contact surface 6810 of the support apparatus faces the viewer. Support apparatus 6800 differs from other embodiments described above in that a plurality of interface features 6896 are disposed along the first tissue contact surface in the form of an arrangement of raised bumps or protrusions extending away from the support apparatus and toward the target tissue during use in a surgical environment. The interface features 6896 can be included to further modify tissue interface characteristics during use, such as to increase purchase between the first contact surface and the tissue to additional enhance retractor functionality. The interface features 6896 can be provided in many different forms and variations from than the raised bumps or protrusions shown in the example embodiment 6800. For instance, the pattern, frequency, density and arrangements of the raised bumps or protrusions themselves can be varied to additionally modify interface characteristics and tissue purchase, as well as other characteristics such as the height, shape, size of the protrusions.

Further, it is understood that many other options and variations can be included in various support apparatus configurations that can modify tissue engagement during use when coupled with a surgical tool, which do not depart from the scope described herein or from aspects and features described herein along with embodiments for the support apparatus. Other example variations of the support apparatus that can also modify tissue interface characteristics include, for instance, the texture of the first tissue contact surface, the type of material that engages the tissue (e.g., durometer and flexibility), the surface area of the contact surface, adhesion characteristics of the surface, and so on. Further, as noted above along with describing the support apparatus 5800, many options can also be included for attaching and retaining the support apparatus to the surgical tool when coupled to it, which likewise fall within the scope of the aspects and features described herein for embodiments of the support apparatus embodiments shown and described. As a further example pertaining to optional attachment/retention features, the support apparatus 6800 shown in FIG. 22 includes an attachment/retention hole 6898 at the proximal end of each of the first and second sleeves 6820, 6870, which can engage a pin either existing in the retractor tool or that can attach to the corresponding retractor blade for each sleeve to provide enhanced attachment and support during use.

It is further understood that many options can be included pertaining to the shape and structure of the flexible contact member, which are also included within the scope of aspect and features of the embodiments described herein. As an example, referring to FIG. 23, an embodiment of a support apparatus 7800 is shown that has a unitary, uninterrupted configuration for the flexible contact member 7890. Such a configuration can provide advantages in certain instances in which it is beneficial to engage tissue with a large surface area and without significant concern regarding permeability or tissue purchase, such as applying significant holding force against a tissue for an extended period to maintain surgical access while avoiding any damage to the engaged tissue.

Figure 24:
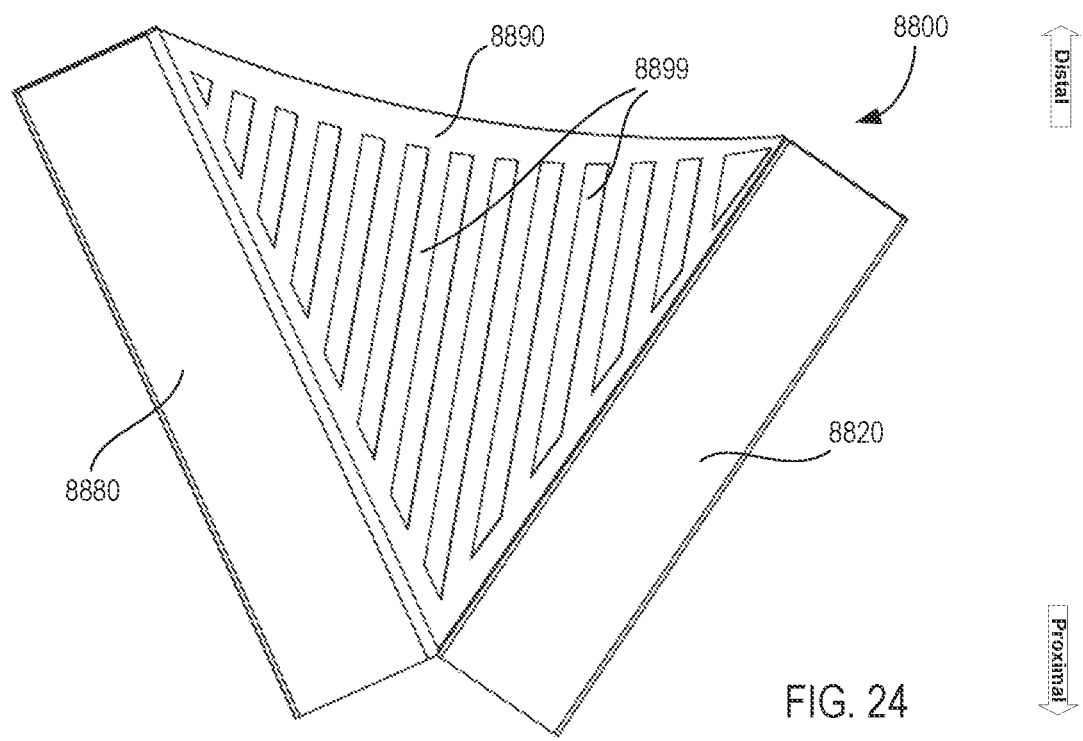
Figure 25:
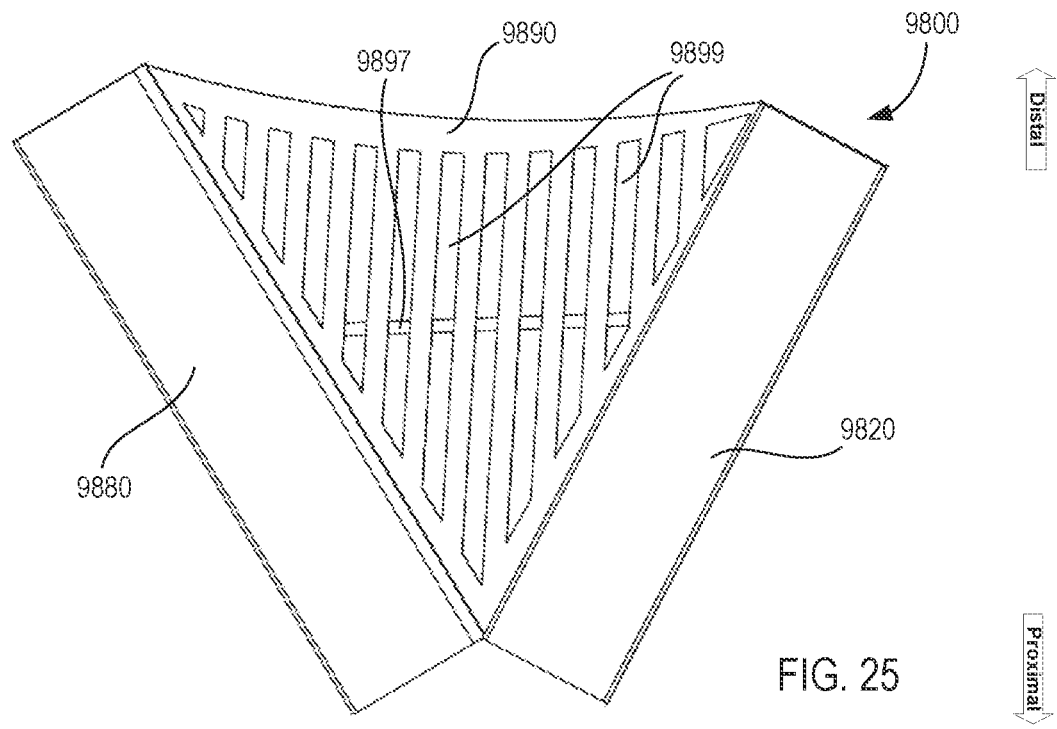

Referring to FIGS. 24 and 25, embodiments 8800 and 9800 of a support apparatus are shown that each have different structural arrangements and interface patterns for the flexible contact member 8890, 9890, which are additional variations and options that can modify tissue interface characteristics during use. Referring to FIG. 24, the flexible contact member 8890 for support apparatus 8800 includes a pattern of slots 8899 that are generally oriented in a proximal to distal direction with respect to the instrument when coupled to it as opposed to mesh, spiderweb or unitary sheet-like configurations described above along with other embodiments. Such an arrangement can provide advantages for engaging certain tissues in which modifying engagement with respect to directional flexibility and/or directional tissue engagement can be beneficial. For example, flexible contact member 8890 can provide enhanced engagement with respect to fibrous tissues or stringy tissues having a bundle of elongate member extending in a general direction when engaging the tissue in a direction generally perpendicular to the tissue orientation.

As another example, flexible contact member 8890 can have greater flexibility in a direction normal to the first tissue contact surface of the flexible contact member based on the orientation of the slots 8899. As such, the flexible contact member 8890 can have greater flexibility to flex or bow away from tissue being engaged at central portions of the flexible contact member 8890, and less flexibility along border portions of the flexible contact member. Such an arrangement can provide benefits in many circumstances, such as providing greater gripping ability and tissue purchase along with bowing around, or contouring against an engaged tissue, or for forming a pouch to cradle a tissue being lifted or moved.

Referring to FIG. 25, support apparatus 9800 is generally the same as support apparatus 8800, except that a cross support 9897 is formed across a mid-portion of the flexible contact member 9890 in a direction normal to the orientation of the slots 9899. As such, the support apparatus 9800 can provide similar advantages as support apparatus 8800. However, the cross support 9897 can limit flexibility to bow or contour about tissue being engaged. This can be beneficial in various circumstances, such as when engaging small tissue pieces that can pass through the slots 9899 if significantly bowed.

While various embodiments have been described above, it should be understood that they have been presented by way of example only, and not limitation. Where methods and/or schematics described above indicate certain events and/or flow patterns occurring in certain order, the ordering of certain events and/or operations may be modified. While the embodiments have been particularly shown and described, it will be understood that various changes in form and details may be made.

For example, any of the instruments described herein (and the components therein) are optionally parts of a surgical assembly that performs minimally invasive surgical procedures, and which can include a patient-side cart, a series of kinematic linkages, a series of cannulas, or the like. Thus, any of the instruments described herein can be used in any suitable surgical system, such as the MIRS system 1000 shown and described above. Moreover, any of the instruments shown and described herein can be used to manipulate target tissue during a surgical procedure. Such target tissue can be cancer cells, tumor cells, lesions, vascular occlusions, thrombosis, calculi, uterine fibroids, bone metastases, adenomyosis, or any other bodily tissue. The presented examples of target tissue are not an exhaustive list. Moreover, a target structure can also include an artificial substance (or non-tissue) within or associated with a body, such as for example, a stent, a portion of an artificial tube, a fastener within the body or the like.

For example, any of the tool members can be constructed from any material, such as medical grade stainless steel, nickel alloys, titanium alloys, or the like. Further, any of the links, tool members, tension members, or components described herein can be constructed from multiple pieces that are later joined together. For example, in some embodiments, a link can be constructed by joining together separately constructed components. In other embodiments, however, any of the links, tool members, tension members, or components described herein can be monolithically constructed.

Although various embodiments have been described as having particular features and/or combinations of components, other embodiments are possible having a combination of any features and/or components from any of embodiments as discussed above. Aspects have been described in the general context of medical devices, and more specifically surgical instruments, but inventive aspects are not necessarily limited to use in medical devices.

What is claimed is:

1. An apparatus, comprising:
   a first blade;
   a second blade;
   a clevis, the first blade and the second blade each being rotatably coupled to the clevis such that the second blade can be moved relative to the first blade between a first orientation and a second orientation, a first contact surface of the first blade being spaced apart from a second contact surface of the second blade by a gap; and
   a support structure including a first connector, a second connector, and a flexible contact member,
   the first connector including an elongate portion configured to extend along a length of the first blade and including a protrusion extending outwardly therefrom and configured to be received through a slot in the first blade,
   the second connector including a sleeve configured to receive the second blade, and
   the support structure configured to be coupled to the first blade and the second blade, the flexible contact member being movable between a collapsed configuration when the second blade is in the first orientation and an expanded configuration when the second blade is in the second orientation, at least a portion of the flexible contact member being within the gap when the flexible contact member is in the collapsed configuration.

2. The apparatus of claim 1, wherein the first blade and the second blade are aligned when the second blade is in the first orientation such that the first blade and the second blade can be advanced through a cannula.

3. The apparatus of claim 1, wherein the first contact surface and the second contact surface are parallel and a rotation of the second blade relative to the first blade is about an axis perpendicular to the first contact surface.

4. The apparatus of claim 1, wherein:
   the elongate portion of the first connector is configured to be placed in contact with a portion of the first contact surface; and
   the second connector is configured to be placed about a portion of the second contact surface.

5. The apparatus of claim 1, further comprising:
a third blade, the third blade including a flat surface; and
the flexible contact member is configured to extend across the flat surface of the third blade when the second blade is in the second orientation.

6. The apparatus of claim 1, further comprising:
a third blade;
the support structure further comprises a third connector configured to be coupled to a portion of the third blade; and
the flexible contact member comprises a first portion coupled to the first connector and the third connector, and a second portion coupled to the second connector and the third connector.

7. The apparatus of claim 1, wherein:
the sleeve of the second connector comprises a retention portion configured to engage the second blade to retain the second connector about the second contact surface.

8. The apparatus of claim 7, wherein:
on the condition that the second blade is received within the second connector, the retention portion interferes with the second blade to limit movement of the second connector from the second blade.

9. The apparatus of claim 7, wherein:
the sleeve of the second connector comprises an interior dimension less than an exterior dimension of the second blade.

10. The apparatus of claim 1, wherein the flexible contact member comprises a plurality of elongate connectors forming an interlaced structure with each other, the interlaced structure extending between the first connector and the second connector.

11. The apparatus of claim 1, wherein:
the first connector is configured to be removably coupled to the first blade, and
the second connector is configured to be removably coupled to the second blade.

12. An endoscopic surgical tissue retractor, comprising:
a first blade having a first contact surface;
a second blade having a second contact surface, the first contact surface and the second contact surface being parallel;
a clevis being rotatably coupled to the first blade and the second blade such that the second blade can be rotated relative to the first blade between a first orientation and a second orientation about an axis that is perpendicular to the first contact surface and the second contact surface; and
a flexible contact member coupled to a first removable connector and a second removable connector, the first removable connector is configured to be removably mated to the first blade and has an inner height sized to form a retention member between the first removable connector and the first blade and the second removable connector is configured to be removably mated to the second blade and has an inner height sized such that a retention member is formed between second removable connector and the second blade,
the flexible contact member being movable between a collapsed configuration when the second blade is in the first orientation and an expanded configuration when the second blade is in the second orientation,
wherein the first blade, the second blade, and the flexible contact member each collapse such that the first blade, the second blade, and the flexible contact member are configured to advance through a cannula.

13. The endoscopic surgical tissue retractor of claim 12, wherein:
the first removable connector is a first sleeve configured to be placed about a portion of the first blade; and
the second removable connector is a second sleeve configured to be placed about a portion of the second blade.

14. The endoscopic surgical tissue retractor of claim 12, wherein:
the first removable connector comprises a first retention portion that wraps around a portion of the first blade to retain the first removable connector about the first contact surface; and
the second removable connector comprises a retention portion that wraps around a portion of the second blade to retain the second removable connector about the second contact surface.

15. The endoscopic surgical tissue retractor of claim 12, further comprising:
a third blade having a third removable connector configured to be placed about a portion of the third blade, wherein the flexible contact member is coupled to the third removable connector.

16. The endoscopic surgical tissue retractor of claim 12, wherein:
the first removable connector has an interior dimension less than an exterior dimension of the first blade, and
the second removable connector has an interior dimension less than an exterior dimension of the second blade.

* * * * *